(12) United States Patent
Dhodapkar et al.

(10) Patent No.: US 7,837,990 B2
(45) Date of Patent: Nov. 23, 2010

(54) IN VIVO EXPANDED NKT CELLS AND METHODS OF USE THEREOF

(75) Inventors: Madhav V Dhodapkar, New York, NY (US); Ralph M. Steinman, Westport, CT (US)

(73) Assignees: The Rockefeller University, New York, NY (US); Kyowa Hakko Kirin, Co., Ltd., Tokyo (JP)

( * ) Notice: Subject to any disclaimer, the term of this patent is extended or adjusted under 35 U.S.C. 154(b) by 473 days.

(21) Appl. No.: 11/378,257

(22) Filed: Mar. 20, 2006

(65) Prior Publication Data

US 2006/0216316 A1 Sep. 28, 2006

Related U.S. Application Data

(60) Provisional application No. 60/665,356, filed on Mar. 28, 2005.

(51) Int. Cl.
C12N 5/0784 (2010.01)
A61K 35/00 (2006.01)

(52) U.S. Cl. .................................. 424/93.71; 435/377

(58) Field of Classification Search ....................... None
See application file for complete search history.

(56) References Cited

U.S. PATENT DOCUMENTS

| 5,405,772 A | 4/1995 | Ponting ................. 435/240.31 |
| 2002/0164331 A1* | 11/2002 | Exley et al. ............... 424/144.1 |
| 2003/0157135 A1* | 8/2003 | Tsuji et al. ............... 424/278.1 |

FOREIGN PATENT DOCUMENTS

| WO | WO 93/20185 | 10/1993 |
| WO | WO 95/00632 | 1/1995 |
| WO | WO 95/06112 | 3/1995 |

OTHER PUBLICATIONS

Mortreux et al, Leukemia, 2003, vol. 17, , pp. 26-38.*
Bender, A. et al. "Improved Methods for the Generations of Dendritic Cells from NonProliferating Progenitors in Human Blood," *J. Immunol. Methods* 196 121-135 (1996).
O'Doherty, U. et al., "Dendritic Cells Freshly Isolated from Human Blood Express CD4 and Mature into Typical Immunostimulatory Dendritic Cells After Culture in Monocyte-Conditioned Medium," *J. Exp. Med.* 178: 1067-1078 (1993).
Bonifaz, L. et al., "Efficient Targeting of Protein Antigen to the Dendritic Cell Receptor DEC-205 in the Steady State Leads to Antigen Presentation on Major Histocompatibility Complex Class I Products and Peripheral CD8+T Cell Tolerance," *J. Exp. Med.* 196(12) 1627-1638 (2002).
Manavalan, J.S., et al. "High Expression of ILT3 and ILT4 is a General Feature of Tolerogenic Dendritic Cells," *Transpl. Immunol.* 11: 245-258 (2003).
Romani, N. et al., "Proliferating Dendritic Cell Progenitors in Human Blood," *J. Exp. Med.* 180: 83-93 (1994).

O'Doherty, U. et al. "Human Blood Contains Two Subsets of Dendritic Cells, One Immunologically Mature and the Other Immature," *Immunology* 82 487-493, (1994).
Steinman, R. M., et al., "Tolerogenic Dendritic Cells" *Annu. Rev. Immunol.* 21, 685-711, (2003).
Banchereau, J., et al., "Immunobiology of Dendritic Cells," *Annu. Rev. Immunol.*, 18,767-811, (2000).
Mellman, I. et al., "Dendritic Cells: Specialized and Regulated Antigen Processing Machines," *Cell* 106, 255-258 (2001).
Steinman, R. M. et al., "Avoiding Horror Autotoxicus: The Importance of Dendritic Cell in Peripheral T Cell Tolerance," *Cell Proc. Natl. Acad. Sci. USA* 99, 351-358, (2002).
Brimnes, M. K., et al., "Influenza Virus-Induced Dendritic Cell Maturation is Associated with the Induction of Strong T Cell Immunity to a Coadministered, Normally Nonimmunogenic Protein," *J. Exp. Med.* 198,133-144, (2003).
Regnault, A. et al. "FCγ Receptor-Mediated Induction of Dendritic Cell Maturation and major Histocompatibility Complex Class I-Restricted Antigen Presentation After Immune Complex Internalization," *J. Exp. Med.* 189, 371-380 (1991).
Ravetch, J. V. et al., "IgG Fc Receptors", *Annu. Rev. Immunol.*, 19, 275-290, (2001).
Bolland, S. et al. "Genetic Modifiers of Systemic Lupus Erythematosus in FcγRIIB -/- Mice," *J. Exp. Med.* 195, 1167-1174 (2002).
Bolland, S. et al. "Spontaneous Autoimmune Disease in FcγRIIB-Deficient Mice Results from Strain-Specific Epistasis", *Immunity* 13, 277-285 (2000).
Clynes, R. A. et al. "Inhibitory Fc Receptors Moduclate in vivo Cytoxicity Against Tumor Targets", *Nat. Med.* 6(4), 443-446 (2000).
Bolland,S. et al., "SHIP Modulates Immune Receptor Responses by Regulating Membrane Association of Btk", *Immunity* 8, 509-516, (1998).
Bolland, S. et al., "Inhibitory Pathways Triggered by ITIM-Containing Receptors," *Adv. Immunol.*, 72, 149-177, (1999).
Amigorena, S. "Fcγ Receptors and Cross-Presentation in Dendritic Cells," *J. Exp. Med.* 195, F1-F3, (2002).
Dhodapkar, K. et al. "Antitumor Monoclonal Antibodies Enhance Cross-Presentation of Cellular Antigens and the Generation of Myeloma-Specific Killer T Cells by Dendritic Cells," *J. Exp. Med.* 195,125-133 (2002).
Selenko, N. et al. "Cross-Priming of Cytotoxic T Cells Promoted by Apoptosis-Inducing Tumor Cell Reactive Antibodies?" *J. Clin. Immunol.* 22, 124-130, (2002).
Kita, H. et al. "Identification of HLA-A2-Restricted CD8+ Cytotoxic T Cell Responses in Primary Biliary Cirrhosis: T Cell Activation is Augmented by Immune Complexes Cross-Presented by Dendritic Cells," *J. Exp. Med.* 195,113-123, (2002).
Nagata, Y. et al. "Differential Presentation of a Soluble Exogenous Tumor Antigen, NY-ESO-1, by Distinct Human Dendritic Cell Populations," *Proc. Natl. Acad. Sci. USA 99*, 10629-10634, (2002).

(Continued)

*Primary Examiner*—Karen A Canella
(74) *Attorney, Agent, or Firm*—Fox Rothschild LLP; Gerard P. Norton

(57) ABSTRACT

This invention relates to the in vivo expansion of NKT cells by their exposure to mature dendritic cells expressing α-galactosyl ceramide and to methods of use thereof in modulating immune responses, such as anti-cancer responses, and enhancing memory responses.

18 Claims, 13 Drawing Sheets

OTHER PUBLICATIONS

Dhodapkar, M. V. et al. "T Cells from the Tumor Microenvironment of Patients with Progressive Myeloma can Generate Strong, Tumor-Specific Cytolytic Responses to Autologous, Tumor-loaded Dendritic Cells," *Proc. Natl. Acad. Sci.* 99,13009-13013, (2002).

Rafiq, K. et al. "Immune Complex-Mediated Antigen Presentation Induces Tumor Immunity," *J. Clin. Invest.* 110, 71-79, (2002).

Gil-Torregrosa, B. C. et al., "Control of Cross-Presentation During Dendritic Cell Maturation," *Eur. J. Immunol.* 34,398-407, (2004).

Rodriguez, A. et al., "Selective Transport of Internalized Antigens to the Cytosol for MHC Class I Presentation in Dendritic Cells", *Nat. Cell Biol.* 1, 362-368, (1999).

Sedlik, C. et al., "A Critical Role for Syk Protein Tyrosine Kinase in Fc Receptor-Mediated Antigen Presentation and Induction of Dendritic Cell Maturation," *J. Immunol.* 170, 846-852, (2003).

Akiyama, K. et al. "Targeting Apoptotic Tumor Cells to FcγR Provides Efficient and Versatile Vaccination Against Tumors by Dendritic Cells," *J. Immunol.* 170,1641-1648, (2003).

Ravetch, J. V. "A Full Complement of Receptors in Immune Complex Diseases," *J. Clin. Invest.* 110, 1759-1761, (2002).

Kalergis, A. M. et al. "Inducing Tumor Immunity Through the Selective Engagement of Activating Fcγ Receptors on Dendritic Cells," *J. Exp. Med.* 195, 1653-1659, (2002).

Jonuleit, H. et al., "Pro-inflammatory Cytokines and Prostaglandins Induce Maturation of Potent Immunostimulatory Dendritic Cells Under Fetal Calk Serum-Free Conditions," *Eur. J. Immunol.* 27, 3135-3142, (1997).

Sallusto, F., et al., "Efficient Presentation of Soluble Antigen by Cultured Human Dendritic Cells is Maintained by Granulocyte/Macrophage Colony-Stimulating Factor Plus Interleukin 4 and Downregulated by Tumor Necrosis Factor," *J. Exp. Med.* 179,1109-1118, (1994).

Bave, U., et al., "FcγRIIa is Expressed on Natural IFN-α-Producing Cells (Plasmacytoid Dendritic Cells) and is Required for the IFN-α Production Induced by Apoptotic Cells Combined with Lupus IgG," *J. Immunol.* 171, 3296-3302, (2003).

Schifferli, J. A. et al., "Physiological and Pathological Aspects of Circulating Immune Complexes," *Kidney Int.* 35, 993-1003, (1989).

Mustafa, A.S., et al., "BCG Induced CD4+Cytotoxic T Cells From BCG Vaccinated Healthy Subjects: Relation Between Cytotoxicity and Suppression In Vitro," *Clin. Exp. Immunol.*, 69, 255-262, (1987).

Kaliński, P., et al. "Prostaglandin $E_2$ is a Selective Inducer of Interleukin-12 p40 (IL-12p40) Production and an Inhibitor of Bioactive IL-12p70 heterodimer," *Blood*, 97, 3466-3469, (2001).

Heath, W. R. et al., "Cross-Presentation, Dendritic Cells, Tolerance and Immunity", *Annu. Rev. Immunol.* 19, 47-64, (2001).

Wardemann, H., et al., "Predominant Autoantibody Production by Early Human B Cell Precursors," *Science*, 301,1374-1377, (2003).

Li, X., et al. "A Novel Polymorphism in the Fcγ Receptor IIB (CD32B) Transmembrane Region Alters Receptor Signaling," *Arthritis Rheum.* 48, 3242-3252, (2003).

Su, K. et al., "A Promoter Haplotype of the Immunoreceptor Tyrosine-Based Inhibitory Motif-Bearing FcγRIIb Alters Receptor Expression and Associates with Autoimmunity. I. Regulatory FCGR2B Polymorphisms and Their Association with Systemic Lupus Erythematosus," *J. Immunol.* 172, 7186-7191, (2004).

Fukuyama, H. et al., "The Inhibitory Fcγ Receptor Modulates Autoimmunity by Limiting the Accumulation of Immunoglobulin G+ Anti-DNA Plasma Cells", *Nat. Immunol.* 6(1), 99-106 (2005).

McGaha, T. L. et al., "Restoration of Tolerance in Lupus by Targeted Inhibtory Receptor Expression", *Science*, in press, 307: 590-593, (2005).

Weng, W. K. et al. "Two Immunoglobulin G Fragment C Receptor Polymorphisms Independently Predict Response to Rituximab in Patients with Follicular Lymphoma," *J. Clin. Oncol.* 21,3940-3947, (2003).

Huguenin, P., et al., "Concomitant Cisplatin Significantly Improves Locoregional Control in Advanced Head and Neck Cancers Treated with Hyperfractionated Radiotherapy," *J. Clin. Oncol.* 22,4665-4672, (2004).

Godfrey, D.I., et al., Going Both Ways: Immune Regulation Via CD1d-Dependent NKT Cells. *J. Clin. Invest.* 114:1379-1388 (2004).

Brigl, M., et al., "CD1: Antigen Presentation and T Cell Function," *Annu. Rev. Immunol.* 22:817-890 (2004).

Kawano, T., et al. "CD1d-Restricted and TCR-Mediated Activation of Valpha14 NKT Cells by Glycosylceramides," *Science.* 278:1626-1629 (1997).

Stetson, D.B., et al. "Constitutive Cytokine mRNAs Mark Natural Killer (NK) and NK T Cells Poised for Rapid Effector Function," *J. Exp. Med.* 198:1069-1076 (2003).

Eberl, G., et al., "Selective Induction of NK Cell Proliferation and Cytotoxicity by Activated NKT Cells," *Eur. J. Immunol.* 30:985-992, (2000).

Smyth, M.J., et al., "Sequential Production of Interferon-Gamma by NK1.1 T Cells and Natural Killer Cells is Essential for the Antimetastatic Effect of Alpha-Galactosylceramide," *Blood*, 99:1259-1266, (2002).

Eberl, G., P. et al., "Selective Bystander Proliferation of Memory CD4 and CD8 T Cells Upon NK T or T Cell Activation," *J. Immunol.* 165:4305-4311 (2000).

Toura, I., et al., "Cutting Edge: Inhibition of Experimental Tumor Metastasis by Dendritic Cells Pulsed With α-Galactosylceramide," *J. Immunol.* 163:2387-2391 (1999).

Smyth, M. J., et al., "NKT cells—conductors of tumor immunity?" *Curr. Opin. Immunol.* 14:165-171 (2002).

Fujii, S., K. et al. "Prolonged IFN-Gamma-Producing NKT Response Induced with Alpha-Galactosylceramide-Loaded DCs," *Nat. Immunol.* 3:867-874 2002.

Hayakawa, Y., et al., "α-Galactosylceramide (KRN7000) Suppression of Chemical- and Oncogenedependent Carcinogenesis," *Proc. Natl. Acad. Sci. USA.* 100:9464-9469 (2003).

Hayakawa, Y., et al., "IFN-Gamma-Mediated Inhibition of Tumor Angiogenesis by Natural Killer T-Cell Ligand, α-Galactosylcer-Amide," *Blood.* 100:1728-1733 (2002).

Swann, J., et al., "Regulation of Antitumour Immunity by CD1d-Restricted NKT Cells," *Immunol. Cell Biol.* 82:323-331 (2004).

Stewart, T.J., et al., "Inhibition of Early Tumor Growth Requires Jα18-Positive (Natural Killer T) Cells," *Cancer Res.*, 63:3058-3060 (2003).

Crowe, N.Y., et al., "A Critical Role for Natural Killer T Cells in Immunosurveillance of Methylcholanthreneinduced Sarcomas," *J. Exp. Med.* 196:119-127 (2002).

Godfrey, D.I., et al., "NKT cells: what's in a name?" *Nat. Rev. Immunol.* 4:231-237 (2004).

Tahir, S. M. et al., "Loss of IFN-Gamma Production by Invariant NK T Cells in Advanced Cancer," *J. Immunol.* 167: 4046-4050 (2001).

Metelitsa, L.S, et al., "Human NKT Cells Mediate Antitumor Cytotoxicity Directly by Recognizing Target Cell CD1d With Bound Ligand or Indirectly by Producing IL-2 to Activate NK Cells," *J. Immunol.* 167:3114-3122 (2001).

Dhodapkar, M. V., et al., "A Reversible Defect in Natural Killer T Cell Function Characterizes the Progression of Premalignant to Malignant Multiple Myeloma," *J. Exp. Med.* 197:1667-1676 (2003).

Giaccone, G., et al., "A Phase I Study of the Natural Killer T-Cell Ligand α-galactosylceramide (KRN7000) in Patients With Solid Tumors," *Clin. Cancer Res.*, 8:3702-3709 (2002).

Nieda, M., et al., "Therapeutic Activation of Vα24+Vβ11+NKT Cells in Human Subjects Results in Highly Coordinated Secondary Activation of Acquired and Innate Immunity," *Blood.* 103:383-389 (2004).

Fujii, S., et al., "Detection and Activation of Human Vα24 Natural Killer T Cells Using α-Galactosyl Ceramide-Pulsed Dendritic Cells," *J. Immunol. Methods.* 272:147-159 (2003).

Crowe, N.Y., et al., Glycolipid Antigen Drives Rapid Expansion and Sus-Tained Cytokine Production by NK T Cells. *J. Immunol.* 171:4020-4027 (2003).

Gadola, S.D., et al. Vα24-JαQ-Independent, CD1d-Restricted Recognition of α-Galactosylceramide by Human CD4+and CD8αβ+T Lymphocytes. *J. Immunol.* 168:5514-5520 (2002).

Gumperz, J. E., et al., "Functionally Distinct Subsets of CD1d-Restricted Natural Killer T Cells Revealed by CD1d Tetramer Staining," *J. Exp. Med.* 195:625-636 (2002).

Lee, P.T. et al; "Distinct Functional Lineages of Human Vα24 Natural Killer T Cells," *J. Exp. Med.* 195:637-641 (2002).

Tomura, M., et al., "A Novel Function of Vα14+CD4+NKT Cells: Stimulation of IL-12 Production by Antigen-Presenting Cells in the Innate Immune System," *J. Immunol.* 163:93-101 (1999).

Kitamura, H, et al., "The Natural Killer T (NKT) Cell Ligand α-Galactosylceramide Demonstrates its Immunopotentiating Effect by Inducing Interleukin (IL)-12 Production by Dendritic Cells and IL-12 Receptor Expression on NKT Cells," *J. Exp. Med.* 189:1121-1128 (1999).

Terabe, M, et al., "NKT Cell-Mediated Repression of Tumor Immunosurveillance by IL-13 and the IL-4R-STAT6 Pathway," *Nat. Immunol.* 1:515-520 (2000).

Fujii, S., et al., "Activation of Natural Killer T Cells by α-Galactosylceramide Rapidly Induces the Full Maturation of Dendritic Cells In Vivo and Thereby Acts as an Adjuvant for Combined CD4 and CD8 T Cell Immunity to a Coadministered Protein," *J. Exp. Med.* 198:267-279 (2003).

Fujii, S., et al., "The Linkage of Innate to Adaptive Immunity Via Maturing Dendritic Cells In Vivo Requires CD40 ligation in addition to antigen presentation and CD80/86 costimulation," *J. Exp. Med.* 199:1607-1618 (2004).

Hermans, I. F "NKT Cells Enhance CD4+ and CD8+ T Cell Responses to Soluble Antigen In Vivo Through Direct Interaction with Dendritic Cells," *J. Immunol.* 171:5140-5147 (2003).

Ghendon, Y. "The Immune Response to Influenza Vaccines," *Acta Virol.* 34:295-304 (1990).

Carnaud, C., et al., "Cutting Edge: Cross-Talk Between Cells of the Innate Immune System: NKT Cells Rapidly Activate NK Cells," *J. Immunol.* 163:4647-4650 (1999).

Ferlazzo, G., et al., "NK Cell Compartments and their Activation by Dendritic Cells," *J. Immunol.* 172:1333-1339 (2004).

Martin-Fontecha, A., et al., "Induced Recruitment of NK Cells to Lymph Nodes Provides IFN-Gamma for T(H)1 Priming," *Nat. Immunol.* 5:1260-1265 (2004).

Ho, L.P., et al., "CD4(−)CD8alphaalpha Subset of CD1d-Restricted NKT Cells Controls T Cell Expansion," *J. Immunol.* 172:7350-7358 (2004).

Dhodapkar, M. V., et al., "Rapid Generation of Broad T-Cell Immunity in Humans After a Single Injection of Mature Dendritic Cells," *J. Clin. Invest.* 104:173-180 (1999).

Berzins, S.P., et al., "Systemic NKT Cell Deficiency in NOD Mice is not Detected in Peripheral Blood: Implications for Human Studies," *Immunol. Cell Biol.* 82:247-252 (2004).

Hayakawa, Y., et al., "Antigen-Induced Tolerance by Intrathymic Modulation of Self-Recognizing Inhibitory Receptors," *Nat. Immunol.* 5:590-596 (2004).

Sriram, V., et al., "Inhibition of Glycolipid Shedding Rescues Recognition of a CD1 T Cell Lymphoma by Natural Killer T (NKT) Cells," *Proc. Natl. Acad. Sci. USA.* 99:8197-8202 (2002).

Zhou, D., et al., "Lysosomal glycosphingolipid Recognition by NKT Cells," *Science.* 306:1786-1789 (2004).

Steinman, R.M., et al., "Active Immunization Against Cancer with Dendritic Cells: The Near Future," *Int. J. Cancer.* 94: 459-473 (2001).

Gabrilovich, D. "Mechanisms and Functional Significance of Tumour-Induced Dendritic-Cell Defects," *Nat. Rev. Immunol.* 4:941-952 (2004).

Granelli-Piperno, A., et al. "HIV-1-Infected Monocyte-Derived Dendritic Cells do not Undergo Maturation but can Elicit IL-10 Production and T Cell Regulation," *Proc. Natl. Acad. Sci. USA.* 101:7669-7674 (2004).

Ikarashi, Y., et al. "Dendritic Cell Maturation Overrules H-2D-Mediated Natural Killer T (NKT) Cell Inhibition: Critical Role for B7 in CD1d-Dependent NKT Cell Interferon Gamma Production," *J. Exp. Med.* 194: 1179-1186 (2001).

Thurner, B. et al., "Generation of Large Numbers of Fully Mature and Stable Dendritic Cells from Leukapheresis Products for Clinical Application," *J. Immunol. Methods.* 223:1-15 (1999).

Dhodapkar, M. V. et al., "Antigen-Bearing Immature Dendritic Cells Induce Peptide-Specific CD8+Regulatory T Cells in vivo in Humans," *Blood* 100:174-177 (2002).

Lee, E., et al., "Increased Expression of IL-23p19 and p40 Subunit mRNA in Lesional Skin of Patients with Psoriasis Vulgaris," *J. Exp. Med.* 199:125-130 (2004).

\* cited by examiner

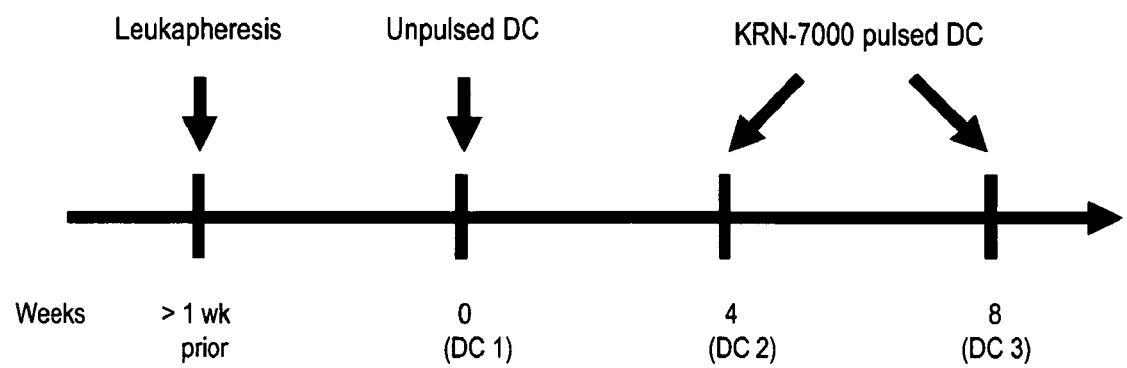
Figure 1. Schema for Clinical Trial

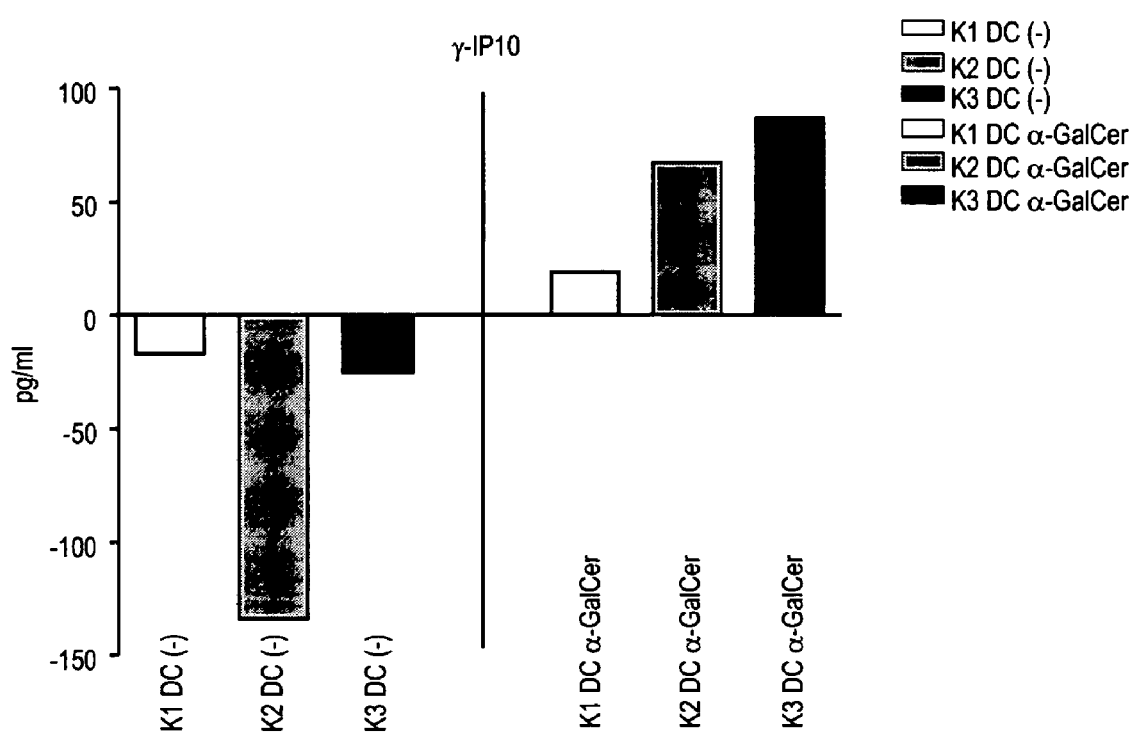

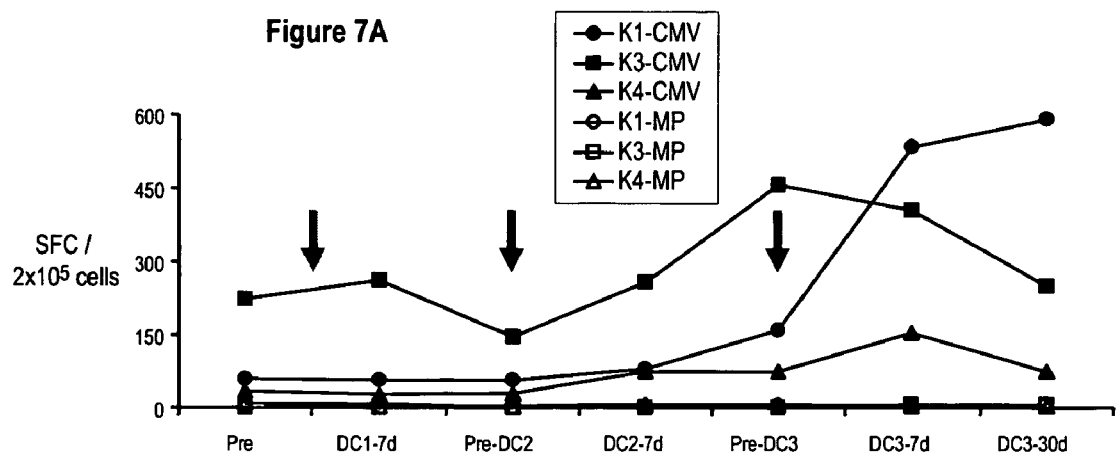
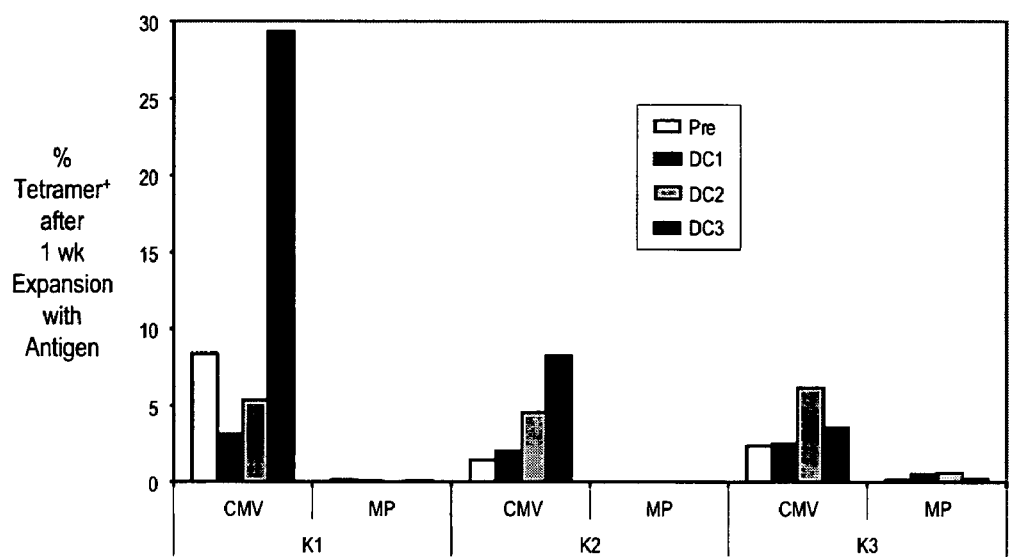

US 7,837,990 B2

IN VIVO EXPANDED NKT CELLS AND METHODS OF USE THEREOF

CROSS-REFERENCE TO RELATED APPLICATIONS

This Application claims priority of U.S. Provisional Application Ser. No. 60/665,356, filed Mar. 28, 2005, which is hereby incorporated in its entirety.

The Research leading to the present invention was supported in part, by National Institutes of Health Grant No. CA 106802. Accordingly, the United States Government has certain rights in the invention.

This invention was made in whole or in part with government support under grant numbers RO1 CA57973-12 and 106802, awarded by National Institute of Health. The government has certain rights in the invention.

FIELD OF THE INVENTION

This invention relates to the expansion of an NKT cell population by exposure to mature dendritic cells in complex with immunogenic compounds, NKT cell stimulation of antigen-specific responses, and methods of use thereof.

BACKGROUND OF THE INVENTION

Immune recognition of pathogens and tumors involves both innate and adaptive arms of the immune system. Natural Killer T (NKT) cells are innate lymphocytes implicated in the control of autoimmunity, and resistance to tumors and pathogens. In contrast to conventional CD4/CD8+ T cells that recognize peptide antigens, NKT cells respond to glycolipid ligands in the context of CD1d. α-galactosyl ceramide (α-GalCer), first isolated from a marine sponge, is a synthetic ligand that is effectively presented on CD1d molecules to both human and murine NKT cells. Activation of NKT cells in mice by injection of α-GalCer is associated with a rapid release of cytokines within hours. Stimulation of NKT cells is followed by downstream activation of NK cells, dendritic cells (DCs) and T cells. α-GalCer mediated NKT activation has been shown to mediate tumor regression in several mouse models. The anti-tumor effects of NKT cells have been demonstrated to be due to several mechanisms including enhancement of immune effectors, as well as anti-angiogenesis. NKT cells also contribute to resistance against spontaneous and carcinogen-induced tumors in mice.

Human NKT cells have been analyzed on the basis of their expression of an invariant T cell receptor (Vα24/Vβ11) and their binding to CD1d-α-GalCer multimers. Human Vα24+ NKT cells can mediate anti-tumor effects in vitro, and a deficiency of NKT cells, or defects in their function, have been described in cancer patients. The availability of α-GalCer as the pharmaceutical grade drug KRN-7000 (Kirin Breweries, Japan) has led to attempts to boost NKT cells in vivo in patients with advanced cancer or healthy volunteers. However, the injection of KRN-7000 alone, or KRN-7000 loaded immature DCs, only leads to transient NKT activation in some individuals.

SUMMARY OF THE INVENTION

This invention provides, in one embodiment, method for expanding an NKT cell population, said method comprising:
  a. contacting a mature dendritic cells with α-galactosyl ceramide; and
  b. contacting the cells in (a) with an NKT cell population, whereby said NKT cell undergoes expansion in said subject to yield at least 100 NKT cells per $1-10^6$ lymphocytes in peripheral blood.

In one embodiment, the contacting is conducted ex vivo or in vivo. In another embodiment, the method further comprises the step of isolating said NKT cells. In another embodiment, the dendritic cells are isolated from a subject with neoplasia or preneoplasia, or in another embodiment, from a subject having, or at enhanced risk of having a carcinoma or myeloma.

In another embodiment, this invention provides a method for expanding an NKT cell population, said method comprising:
  a. contacting a mature dendritic cells with α-galactosyl ceramide; and
  b. contacting the cells in (a) with an NKT cell population in a subject, whereby said NKT cell undergoes expansion in said subject for a period of at least two months, following contact with said cells in (a).

In another embodiment, this invention provides a method of stimulating or enhancing an immune response in a subject, said method comprising:
  a. contacting mature dendritic cells with α-galactosyl ceramide;
  b. contacting the cells in (a) with an NKT cell population in said subject, whereby said NKT cell population undergoes expansion to yield at least 100 NKT cells per $1 \times 10^6$ lymphocytes in peripheral blood of said subject and said NKT cell population participates in said immune response.

In one embodiment, the expanded NKT cell population stimulates or enhances antigen presenting cells. In another embodiment, the method further comprises contacting said culture with a second antigen presenting cell. In one embodiment, the method further comprises the step of contacting the culture with a vaccine, which in one embodiment, comprises antigens derived from a pathogen, or in another embodiment, antigens predominantly or preferentially expressed in neoplastic cells or tissue.

In another embodiment, this invention provides a method for delaying onset, reducing incidence, suppressing or reducing the severity of neoplasia in a subject, comprising the steps of:
  a. contacting mature dendritic cells isolated from a subject having or predisposed to having neoplasia with α-galactosyl ceramide; and
  b. contacting the cells in (a) with an NKT cell population in a subject;

whereby said NKT cells undergo expansion to yield at least 100 NKT cells per $1 \times 10^6$ lymphocytes in the peripheral blood of said subject and said NKT cells participate in an antineoplastic response in said subject.

In another embodiment, this invention provides an in vivo-expanded NKT cell population isolated from a subject, wherein said population is characterized by $CD4^+$, $CD8^+$ or $CD4^-CD8^-$ surface expression and wherein said population is at a concentration of at least 100 NKT cells per $1 \times 10^6$ lymphocytes in the peripheral blood of said subject. In one embodiment, the in vivo-expanded NKT cell population is at a concentration ranging from at least $100-1 \times 10^4$ per $1 \times 10^6$ lymphocytes in said subject.

BRIEF DESCRIPTION OF THE DRAWINGS

FIG. 1 demonstrates a schema for the clinical trial.

DETAILED DESCRIPTION OF THE INVENTION

Figure 2A:
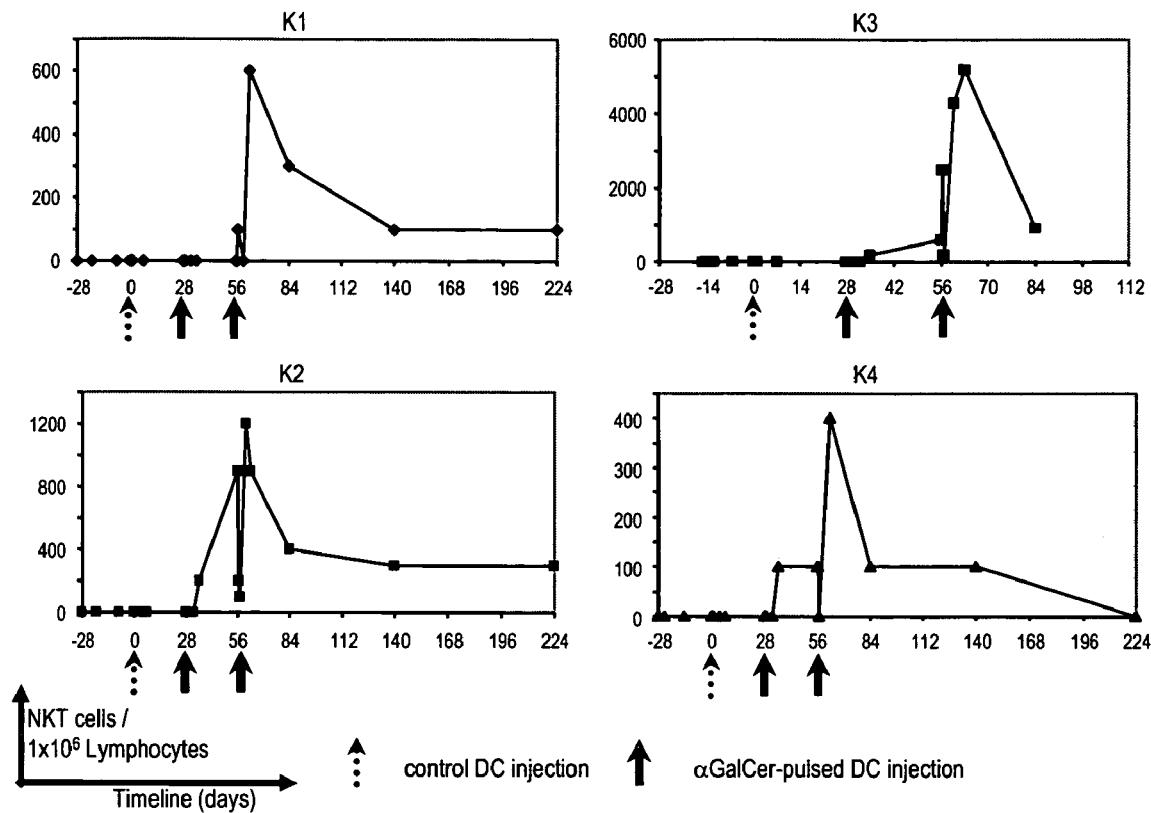
FIG. 2 demonstrates the expansion of NKT cells after injection of α-GalCer pulsed DCs. (A) Kinetics of Vα24+/Vβ11+ NKT cells in blood. The proportion of Vα24+/Vβ11+ NKT cells in blood was monitored before and after DC vaccination. The dates of DC injections are depicted by arrows. (B) Representative FACS plots showing the number of invariant NKT cells before and after DC vaccination. Numbers in upper right quadrant represent percentage NKT/total lymphocytes. (C) Correlation between kinetics of α-GalCer dimer binding cells and invariant TCR+ cells. Dimer positive NKT cells were analyzed based on the co-expression of Vα24 or Vβ11. The data shown are from K3. (D) Representative FACS plots showing the expression of Vα24/Vβ11+ on α-GalCer-CD1d dimer binding cells elicited post vaccination in a patient (K3). A sub-population of Vα24-CD1d dimer+ cells is circled. Note that the Vβ11+ dimer+ populations consist of two distinct subsets. (E) Expansion of invariant NKT cells in the tumor bed. NKT cells in the blood or marrow tumor bed were monitored by flow cytometry.

In one embodiment, this invention provides methods for sustained expansion of human NKT cells, in vivo. In one embodiment, the method makes use of α-GalCer pulsed mature dendritic cells (DCs) for sustained expansion of glycolipid reactive NKT cells.

NKT cell expansion may be induced in human patients, as exemplifed herein, following injection of α-GalCer loaded mature DCs. Remarkably, expansion occurred in subjects previously exposed to chemotherapy, with the expansion lasting several months, post-administration, this despite previous reports of at best transient activation, when human patients were given either α-GalCer alone, or α-GalCer-pulsed immature DCs. Moreover, NKT expansion was feasible in vivo, although NKT cells could not be expanded in vitro from patient samples taken prior to exposure to the α-GalCer loaded mature DCs. Therefore as with peptide antigens, targeting glycolipid antigens to mature DCs leads to enhanced immune activation.

In one embodiment, this invention provides a method for expanding an NKT cell population, said method comprising:
 a. contacting a mature dendritic cells with α-galactosyl ceramide; and
 b. contacting the cells in (a) with an NKT cell population, whereby said NKT cell undergoes expansion in said subject to yield at least 100 NKT cells per $1\times10^6$ lymphocytes in peripheral blood.

In one embodiment, this invention provides a method for expanding an NKT cell population, said method comprising:

a. contacting a mature dendritic cells with α-galactosyl ceramide; and
b. contacting the cells in (a) with an NKT cell population in a subject, whereby said NKT cell undergoes expansion in said subject for a period of at least two months, following contact with said cells in (a).

In one embodiment, the contacting is conducted ex vivo or, in another embodiment, in vitro, or in another embodiment, in vivo.

In one embodiment, dendritic cells (DCs) are contacted with α-GalCer in vitro, and NKT cells are contacted with the dendritic cells in vitro, following which, the NKT cells, DCs, or combination thereof, are administered to a subject.

In another embodiment, the DCs are contacted with α-GalCer in vitro, then administered to a subject, where the NKT cells are then contacted with the dendritic cells in vivo.

In another embodiment, DCs are isolated from a subject, contacted with α-GalCer, and contacted NKT cells ex-vivo, or, in another embodiment, in vivo. In one embodiment, the DCs are autologous, or in another embodiment, syngeneic, or in another embodiment, allogeneic, with respect to the subject to which the DCs are administered.

In one embodiment, the term "dendritic cell" (DC) refers to antigen-presenting cells, which are capable of presenting antigen to T cells, in the context of CD1. In one embodiment, the dendritic cells utilized in the methods of this invention may be of any of several DC subsets, which differentiate from, in one embodiment, lymphoid or, in another embodiment, myeloid bone marrow progenitors.

In one embodiment, the methods of this invention employ a cytokine cocktail for generating mature DCs, which are capable of presenting the antigen to T cells, and promote their expansion. In one embodiment, the cocktail may comprise IL-1β, IL-6, TNF-α and $PGE_2$. In one embodiment, the cocktail may comprise granulocyte-macrophage colony-stimulating-factor (GM-CSF), or in another embodiment, interleukin (IL)-3, which may, in another embodiment, enhance DC survival.

In another embodiment, DCs may be generated from proliferating progenitors isolated from bone marrow. In another embodiment, DCs may be isolated from CD34+ progenitors as described by Caux and Banchereau in Nature in 1992, or from monocytes, as described by Romani et al, J. Exp. Med. 180: 83-93 '94 and Bender et al, J. Immunol. Methods, 196: 121-135, '96 1996. In another embodiment, the DCs are isolated from blood, as exemplified herein, and/or as described for example, in O'Doherty et al, J. Exp. Med. 178: 1067-1078 1993 and Immunology 82: 487-493 1994, all methods of which are incorporated fully herewith by reference.

In one embodiment, the DCs utilized in the methods of this invention may express myeloid markers, such as, for example, CD11c or, in another embodiment, an IL-3 receptor-α (IL-3Rα) chain (CD123). In another embodiment, the DCs may produce type I interferons (IFNs). In one embodiment, the DCs utilized in the methods of this invention express costimulatory molecules. In another embodiment, the DCs utilized in the methods of this invention may express additional adhesion molecules, which may, in one embodiment, serve as additional costimulatory molecules, or in another embodiment, serve to target the DCs to particular sites in vivo, when delivered via the methods of this invention, as described further hereinbelow.

In one embodiment, the DCs may be obtained from in vivo sources, such as, for example, most solid tissues in the body, peripheral blood, lymph nodes, gut associated lymphoid tissue, spleen, thymus, skin, sites of immunologic lesions, e.g. synovial fluid, pancreas, cerebrospinal fluid, tumor samples, granulomatous tissue, or any other source where such cells may be obtained. In one embodiment, the dendritic cells are obtained from human sources, which may be, in another embodiment, from human fetal, neonatal, child, or adult sources. In another embodiment, the dendritic cells used in the methods of this invention may be obtained from animal sources, such as, for example, porcine or simian, or any other animal of interest. In another embodiment, dendritic cells used in the methods of this invention may be obtained from subjects that are normal, or in another embodiment, diseased, or in another embodiment, susceptible to a disease of interest, or in another embodiment, of a particular genetic profile, such as, for example, from an individual which is known to over-express a particular gene, or in another embodiment, under-express a particular gene, or in another embodiment, be from a population typically resistant to a particular infection or disease.

Dendritic cell separation may accomplished in another embodiment, via any of separation methods as is known in the art. In one embodiment, positive and/or negative affinity based selections are conducted. In one embodiment, positive selection is based on CD86 expression, and negative selection is based on GR1 expression.

In another embodiment, the dendritic cells used in the methods of this invention may be generated in vitro by culturing monocytes in presence of GM-CSF and IL-4.

In one embodiment, the dendritic cells used in the methods of this invention may express CD83, an endocytic receptor to increase uptake of the autoantigen such as DEC-205/CD205 in one embodiment, or DC-LAMP (CD208) cell surface markers, or, in another embodiment, varying levels of the antigen presenting MHC class I and II products, or in another embodiment, accessory (adhesion and co-stimulatory) molecules including CD40, CD54, CD58 or CD86, or any combination thereof. In another embodiment, the dendritic cells may express varying levels of CD115, CD14, CD68 or CD32.

In one embodiment, the DCs are matured for effecting the methods of this invention. In one embodiment, the term "mature dendritic cells" refers to a population of dendritic cells with diminished CD115, CD14, CD68 or CD32 expression, or in another embodiment, a population of cells with enhanced CD86 expression, or a combination thereof. In another embodiment, mature dendritic cells will exhibit increased expression of one or more of p55, CD83, CD40 or CD86 or a combination thereof. In another embodiment, the dendritic cells used in the methods of this invention will express the DEC-205 receptor on their surface. In another embodiment, maturation of the DCs may be accomplished via, for example, CD40 ligation, CpG oligodeoxyribonucleotide addition, ligation of the IL-1, TNFα or TOLL like receptor ligand, bacterial lipoglycan or polysaccharide addition or activation of an intracellular pathway such as TRAF-6 or NF-κB. It is to be understood that DC maturation via any of these means, or in combination with the cocktails as described, may be utilized for effecting the methods of this invention and represent embodiments thereof.

In one embodiment, inducing DC maturation may be in combination with endocytic receptor delivery of a preselected antigen. In one embodiment, endocytic receptor delivery of antigen may be via the use of the DEC-205 receptor. In one embodiment, the antigen is α-GalCer, or in another embodiment, is a homologue thereof.

In one embodiment, the maturation status of the dendritic may be confirmed, for example, by detecting either one or more of 1) an increase expression of one or more of p55, CD83, CD40 or CD86 antigens; 2) loss of CD115, CD14, CD32 or CD68 antigen; or 3) reversion to a macrophage phenotype characterized by increased adhesion and loss of veils following the removal of cytokines which promote maturation of PBMCs to the immature dendritic cells, by methods well known in the art, such as, for example, immunohistochemistry, FACS analysis, and others. In another embodiment, the maturation status of the DC is evidenced via NKT cell expansion, as described and exemplified herein.

In one embodiment, the dendritic cells used for the methods of this invention may express, or in another embodiment, may be engineered to express a costimulatory molecule. In one embodiment, dendritic cells used for the methods of this invention are enriched for $CD86^{high}$ or $CD80^{high}$ expression.

In another embodiment, the dendritic cells used in the methods of this invention are selected for their capacity to expand NK T cells. In one embodiment, the DCs are isolated from progenitors or from blood for this purpose. In another embodiment, dendritic cells expressing high amounts of DEC-205/CD205 are used for this purpose.

In one embodiment, the term "contacting a cell" refers herein to both direct and indirect exposure of cell to the indicated item. In one embodiment, contact of DCs with a compound of this invention, an NKT cell, a cytokine or cytokine cocktail, growth factor, or combination thereof, is direct or, in another embodiment, indirect. In one embodiment, contacting a cell may comprise direct injection of the cell through any means well known in the art, such as microinjection. It is also envisaged, in another embodiment, that supply to the cell is indirect, such as via provision in a culture medium that surrounds the cell, or administration to a subject, via any route well known in the art, and as described hereinbelow.

Methods for priming dendritic cells with antigen are well known to one skilled in the art, and may be effected, as described for example Hsu et al., Nature Med. 2:52-58 (1996); or Steinman et al. International application PCT/US93/03141.

In one embodiment, α-GalCer is added to a culture of dendritic cells prior to contact of the dendritic cells with NK T cells, following DC maturation. In one embodiment, α-GalCer is used at a concentration of between about 1 to about 1,000 ng/ml. In one embodiment, α-GalCer is used at a concentration of between about 0.05 to about 200 µg/ml. In one embodiment, 10-50 ng/ml is used. The dendritic cells are, in one embodiment, cultured in the presence of the antigen for a sufficient time to allow for uptake and presentation, prior to, or in another embodiment, concurrent with culture with NK T cells.

Antigenic uptake and processing, in one embodiment, can occur within 24 hours, or in another embodiment, longer periods of time may be necessary, such as, for example, up to and including 4 days or, in another embodiment, shorter periods of time may be necessary, such as, for example, about 1-2 hour periods.

In another embodiment, the NK T cells expanded by the dendritic cells in the methods of this invention are autologous, syngeneic or allogeneic, with respect to the dendritic cells.

In another embodiment, the dendritic cells used in the methods of this invention are isolated from a subject suffering from an autoimmune disease or disorder, cancer, an infection, which in one embodiment, is HIV, mycobacterial or malarial infection.

In another embodiment, the method further comprises the step of isolating the NKT cells.

In one embodiment, the phrase "NKT cell" or "Natural Killer cell", refers to a T cell population that causes, stimulates or contributes to cytokine production, and/or in another embodiment, is cytotoxic. In one embodiment, the NKT cells are a homogenous population, or in another embodiment, a heterogeneous population.

NKT cells are an exceptional subset of mature lymphocytes that bear both NK and T cell receptors. Murine NKT cells express NK1.1 and TCRαβ receptors and are especially dense in the bone marrow and liver. The cells may express a very limited TCR repertoire, which may include an invariant α-chain. The ligand for NKT cells may be non-polymorphic, and a non-classical MHC class I molecule may present a specific antigen processed via a TAP (transporter associated with antigen processing)-independent pathway.

In one embodiment, the antigen is presented in the context of a CD1 molecule, which in one embodiment is CD1d. Activated NK T cells may display an NK-like perform-dependent cytotoxicity against various cells, including tumor cells or cell lines and inhibit tumor metastasis, among other applications, as is described further hereinbelow, and representing embodiments of the methods of this invention.

The T cells of this invention may express CD161 and Vα24i TCR on their cell surface. In one embodiment, the T cells may be classified as $CD161^{high}$ expressors, or in another embodiment, the T cells may be classified as $CD161^{low}$ expressors, or in another embodiment, a combination thereof.

It is to be understood that the NK T cells of this invention, and those obtained via the methods of this invention, may express any number or combination of cell surface markers, as described herein, and as is well known in the art, and are to be considered as part of this invention.

In one embodiment, the T cell subpopulation, are "invariant NK T cells," which may represent a major fraction of the mature T cells in thymus, the major T cell subpopulation in murine liver, and/or up to 5% of splenic T cells.

In another embodiment, the T cell subpopulation may be "non-invariant NK T cells", which may comprise human and mouse bone marrow and human liver T cell populations that are, for example, CD1d-reactive noninvariant T cells which express diverse TCRs, and which can also produce a large amount of IL-4 and IFN-γ. In another embodiment, the NKT cells will bind CD1d-glycolipid multimers, as described and exemplified herein.

In one embodiment, NKT cells are contacted with DCs in vitro, and undergo expansion in culture. In one embodiment, the NKT cells may be obtained by positive selection for expression of CD161 and Vα24i TCR, and in another embodiment, the T cells may be obtained via negative selection procedures, as are well known in the art.

In one embodiment, the NK T cells may be obtained from in vivo sources, such as, for example, peripheral blood, leukopheresis blood product, apheresis blood product, peripheral lymph nodes, gut associated lymphoid tissue, spleen, thymus, cord blood, mesenteric lymph nodes, liver, sites of immunologic lesions, e.g. synovial fluid, pancreas, cerebrospinal fluid, tumor samples, granulomatous tissue, or any other source where such cells may be obtained. In one embodiment, the NK T cells are obtained from human sources, which may be, in another embodiment, from human fetal, neonatal, child, or adult sources. In another embodiment, the NK T cells of this invention may be obtained from animal sources, such as, for example, porcine or simian, or any other animal of interest. In another embodiment, the NK T cells of this invention may be obtained from subjects that are normal, or in another embodiment, diseased, or in another embodiment, susceptible to a disease of interest.

In one embodiment, NKT cell isolation is accomplished at multiple times following the administration of α-GalCer pulsed dendritic cells. In one embodiment, sustained expansion of the NKT cells, as described herein, provides a continued source for isolation of NKT cells. In one embodiment, the NKT cells isolated are CD4+, or in another embodiment, CD8+ or, in another embodiment, CD4−CD8−, and in another embodiment, the relative abundance of each subset of NKT cells is a function of the timing of their isolation, following contact with α-GalCer pulsed dendritic cells.

In one embodiment, the T cells and/or DCs and/or APCs, as described herein, may be isolated from tissue, and, in another embodiment, an appropriate solution may be used for dispersion or suspension, toward this end. In another embodiment, T cells and/or other cells, may be cultured in solution.

Such a solution may be, in another embodiment, a balanced salt solution, such as normal saline, PBS, or Hank's balanced salt solution, or others, each of which represents another embodiment of this invention. The solution may be supplemented, in other embodiment, with fetal calf serum, bovine serum albumin (BSA), normal goat serum, or other naturally occurring factors, and, in another embodiment, may be supplied in conjunction with an acceptable buffer. The buffer may be, in other embodiments, HEPES, phosphate buffers, lactate buffers, or the like, as will be known to one skilled in the art.

In another embodiment, the solution in which the cells may be placed is in medium is which is serum-free, which may be, in another embodiment, commercially available, such as, for example, animal protein-free base media such as X-VIVO 10™ or X-VIVO 15™ (BioWhittaker, Walkersville, Md.), Hematopoietic Stem Cell-SFM media (GibcoBRL, Grand Island, N.Y.) or any formulation which promotes or sustains cell viability. Serum-free media used, may, in another embodiment, be as those described in the following patent documents: WO 95/00632; U.S. Pat. No. 5,405,772; PCT US94/09622. The serum-free base medium may, in another embodiment, contain clinical grade bovine serum albumin, which may be, in another embodiment, at a concentration of about 0.5-5%, or, in another embodiment, about 1.0% (w/v). Clinical grade albumin derived from human serum, such as Buminate® (Baxter Hyland, Glendale, Calif.), may be used, in another embodiment.

In another embodiment, the cells of and for use in this invention may be separated via affinity-based separation methods. Techniques for affinity separation may include, in other embodiments, magnetic separation, using antibody-coated magnetic beads, affinity chromatography, cytotoxic agents joined to a monoclonal antibody or use in conjunction with a monoclonal antibody, for example, complement and cytotoxins, and "panning" with an antibody attached to a solid matrix, such as a plate, or any other convenient technique. In other embodiment, separation techniques may also include the use of fluorescence activated cell sorters, which can have varying degrees of sophistication, such as multiple color channels, low angle and obtuse light scattering detecting channels, impedance channels, etc. It is to be understood that any technique, which enables separation of the cells of or for use in this invention may be employed, and is to be considered as part of this invention.

In another embodiment, the affinity reagents employed in the separation methods may be specific receptors or ligands for the cell surface molecules indicated hereinabove.

In another embodiment, the antibodies utilized herein may be conjugated to a label, which may, in another embodiment, be used for separation. Labels may include, in other embodiments, magnetic beads, which allow for direct separation, biotin, which may be removed with avidin or streptavidin bound to, for example, a support, fluorochromes, which may be used with a fluorescence activated cell sorter, or the like, to allow for ease of separation, and others, as is well known in the art. Fluorochromes may include, in one embodiment, phycobiliproteins, such as, for example, phycoerythrin, allophycocyanins, fluorescein, Texas red, or combinations thereof.

In one embodiment, cell separations utilizing antibodies will entail the addition of an antibody to a suspension of cells, for a period of time sufficient to bind the available cell surface antigens. The incubation may be for a varied period of time, such as in one embodiment, for 5 minutes, or in another embodiment, 15 minutes, or in another embodiment, 30 minutes. Any length of time which results in specific labeling with the antibody, with minimal non-specific binding is to be considered envisioned for this aspect of the invention.

In another embodiment, the staining intensity of the cells can be monitored by flow cytometry, where lasers detect the quantitative levels of fluorochrome (which is proportional to the amount of cell surface antigen bound by the antibodies). Flow cytometry, or FACS, can also be used, in another embodiment, to separate cell populations based on the intensity of antibody staining, as well as other parameters such as cell size and light scatter.

In another embodiment, the labeled cells are separated based on their expression of CD161 and Vα24i TCR. In another embodiment, the cells are separated based on their expression of Vβ11 TCR. In another embodiment, the cells are separated based on their expression of CD4, CD8, or lack of expression of either. In another embodiment, such separation may be conducted as a function of time in culture, or in another embodiment, time post-contact with α-GalCer pulsed DCs.

The separated cells may be collected in any appropriate medium that maintains cell viability, and may, in another embodiment, comprise a cushion of serum at the bottom of the collection tube.

In another embodiment, the culture containing the cells of or for use in this invention may contain other cytokines or growth factors to which the cells are responsive. In one embodiment, the cytokines or growth factors promote survival, growth, function, or a combination thereof. In another embodiment, the culture containing the cells of or for use in this invention may contain polypeptides and non-polypeptide factors.

In another embodiment, the methods of this invention employ the use of immature dendritic cells, which are matured via the addition of factors, as described herein, such as the cytokine cocktail, as described and exemplified herein. In one embodiment, the immature dendritic cells are isolated from a subject with neoplasia or preneoplasia, or in another embodiment, from a subject having, or at enhanced risk of having a carcinoma or myeloma, or in another embodiment, from a subject with an active infection, or in another embodiment, with a latent infection. In one embodiment, the dendritic cells are obtained from a subject who suffers from an acute, or chronic infection or disease.

In one embodiment, the invention provides for the intravenous injection of α-GalCer pulsed DCs to a subject in need. As exemplifed hereinbelow, such injection led to >100 fold increase in circulating NKT cells (FIG. 2A) in subjects with few or no detectable NKT cells prior to injection.

Figure 2B:
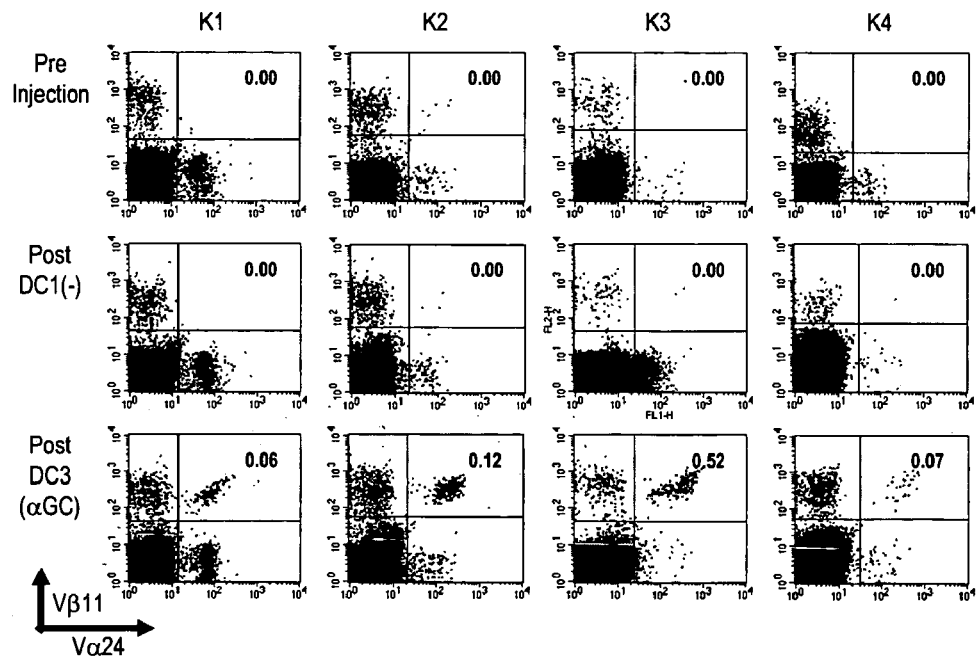
Figure 2C:
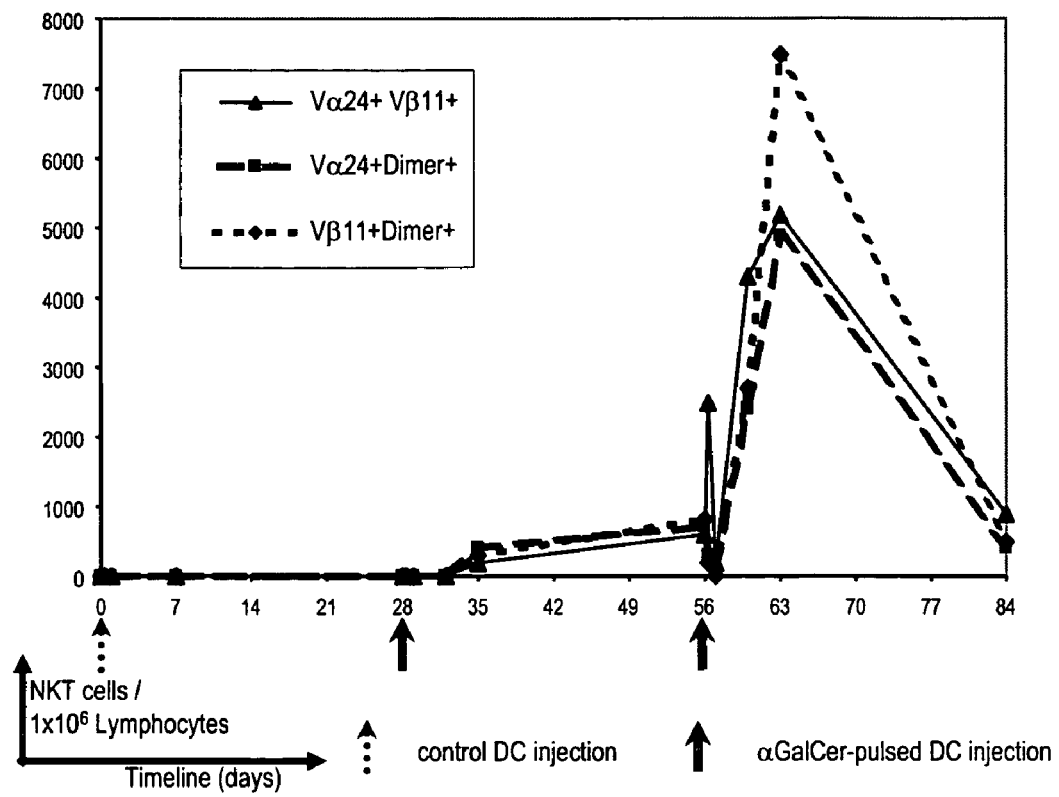
Figure 2D:
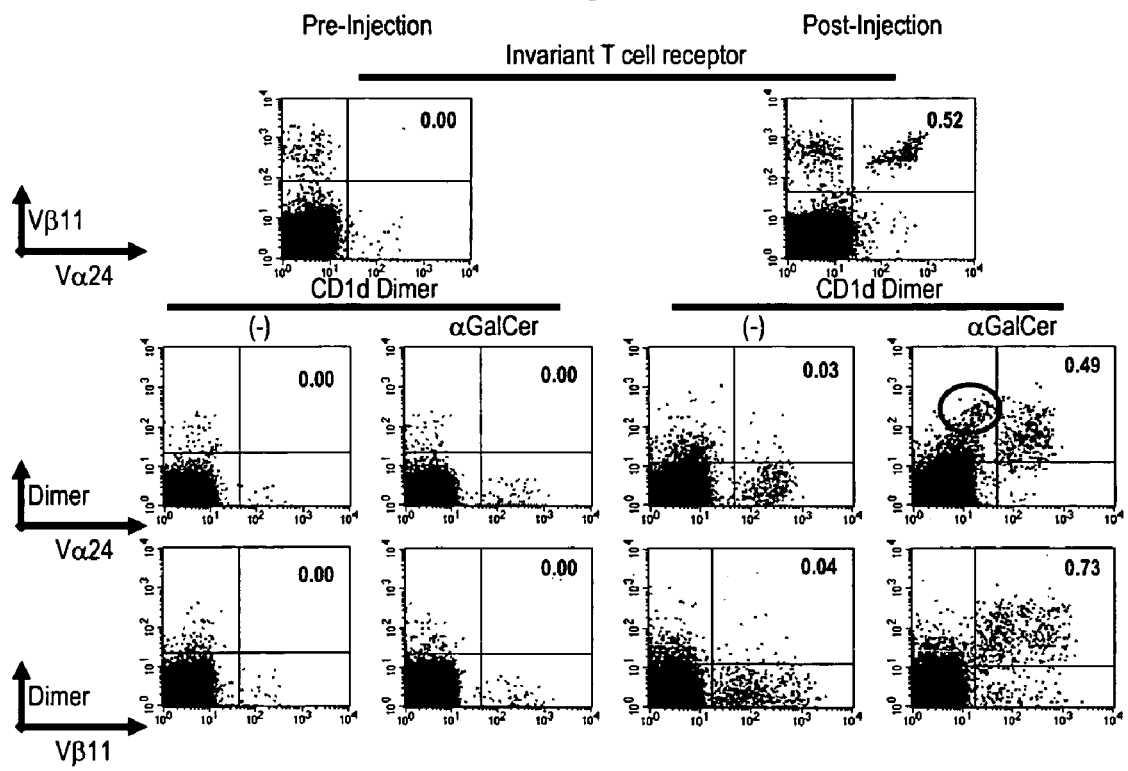
Figure 2E:
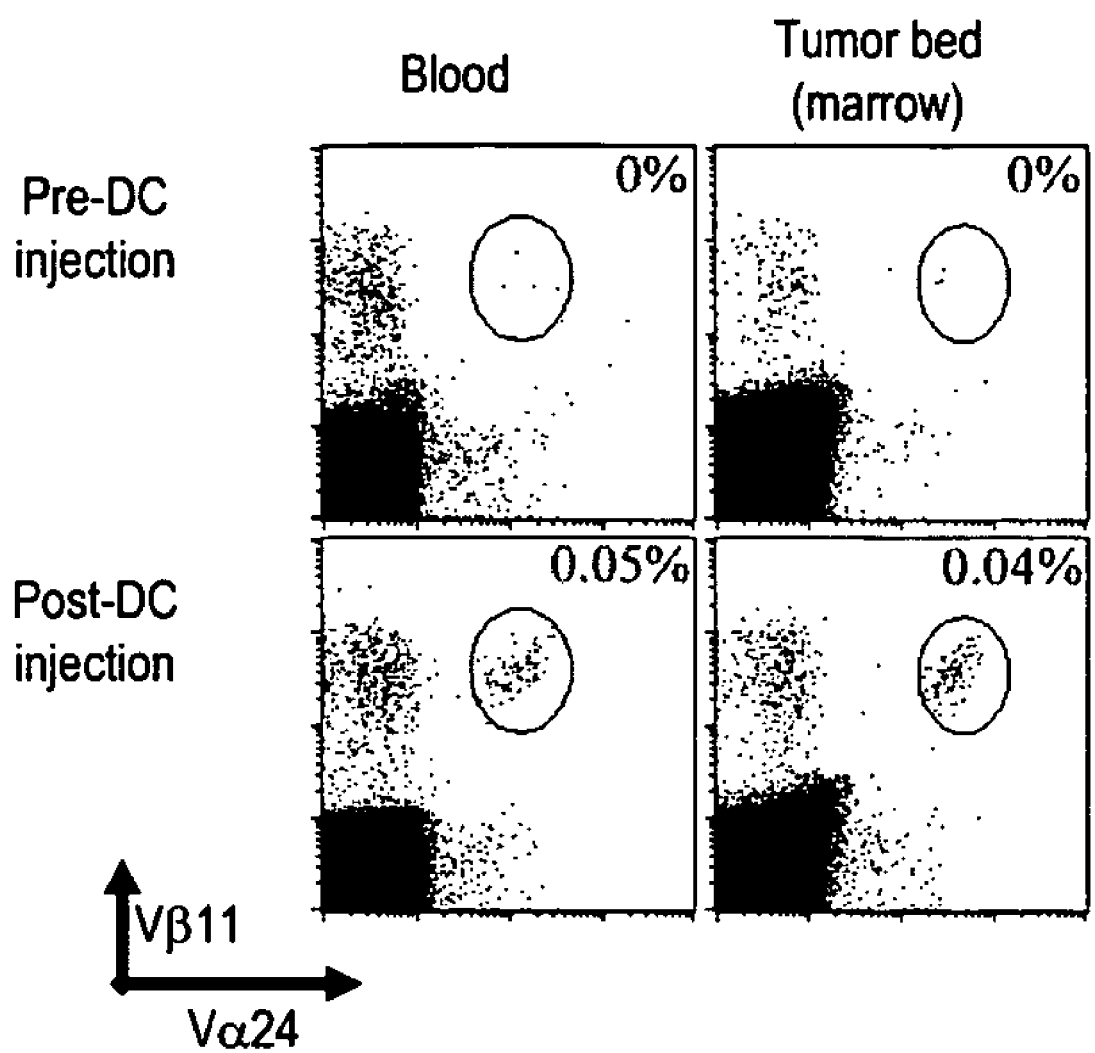

As exemplified herein, this invention provides a method for achieving sustained NKT cell expansion in a subject. The number of NKT cells detected in subjects administered α-GalCer pulsed DCs exceeded at least 80 days, and more than 6 months in some patients, as exemplified herein. Moreover, NKT cells were found in periperhal blood, as well as in the bone marrow tumor bed in myeloma patients evaluated, for sustained periods of time (FIG. 2E).

Thus, in another embodiment, this invention provides for methods for the sustained ability to obtain NKT cells in peripheral blood or other organs, which in one embodiment, are lymphoid organs, such as bone marrow, or in another embodiment, lymph nodes, or in another embodiment, any affected tissue wherein the NKT cells may be found.

In one embodiment, the NKT cells undergo expansion to a concentration ranging from at least $100\text{-}1\times10^4$ per $1\times10^6$ lymphocytes, in vivo in the blood of a subject, wherein the methods of this invention are employed. In one embodiment, the NKT cells undergo expansion to a concentration ranging from at least $1\times10^2$ per $1\times10^6$ lymphocytes, or, in another embodiment, from at least $5\times10^2$ per $1\times10^6$ lymphocytes, or, in another embodiment, from at least $1\times10^3$ per $1\times10^6$ lymphocytes, or, in another embodiment, from at least $5\times10^3$ per $1\times10^6$ lymphocytes, in vivo in the blood of a subject, wherein the methods of this invention are employed. It is to be understood that the methods of this invention contemplate multiple administrations of the α-GalCer pulsed DCs, or NKT cells or antigen presenting cell, or antigen, or combination thereof to a given subject, whereby NKT cell proliferation may exceed by several orders of magnitude, the values exemplified and described herein. In one embodiment, expanded NKT cells may be stored and pooled, and subsequently administered to a subject, at a desired point in time, in order to maximize the number of NKT cells administered to a subject. Such cells may be administered in conjunction with antigen presenting cells, or in another embodiment, peptide, or in another embodiment, a combination thereof, and may serve to maximize the immune response generated in the subject.

In another embodiment, the invention provides a composition or vaccine including, inter alia, α-GalCer pulsed DCs or expanded NKT cells, antigen, other antigen presenting cells, or a combination thereof, as further described herein. In another embodiment, the composition or vaccine may include, inter alia, cytokines, growth factors, adjuvants, or other molecules useful in stimulating immune responses, or a combination thereof.

In one embodiment of the invention, the expanded NKT cells secrete a cytokine.

In one embodiment of the invention, the subject may be immunocompromised. In another embodiment, the subject is infected. In another embodiment, the subject is infected with HIV. In another embodiment, the subject is infected with mycobacteria. In another embodiment, the subject is infected with malaria.

In one embodiment of the invention, the subject is afflicted with cancer. In one embodiment of the invention, the subject is at an elevated risk for cancer. In one embodiment of the invention, the subject has precancerous precursors.

In another embodiment, this invention provides a method for stimulating or enhancing an immune response in a subject, said method comprising:
   a. contacting mature dendritic cells with α-galactosyl ceramide;
   b. contacting the cells in (a) with an NKT cell population in said subject, whereby said NKT cell population undergoes expansion to yield at least 100 NKT cells per $1\times10^6$ lymphocytes in peripheral blood of said subject and said NKT cell population participates in said immune response.

IL-12 p40, IP-10 and MIP-1β were shown herein to increase, following injection of α-GalCer loaded DCs, but not unpulsed DCs in all subjects tested (FIG. 4A-C), which in one embodiment is a reflection of NKT activation and subsequent activation of APCs in vivo. The methods of this invention, in some embodiments, find application in the stimulation of viral antigen specific T cells, for example, T cells specifically recognizing CMVpp65, or other infections wherein persistant antigen may be found within the host, which can in turn be presented on APC's activated by the expanded NKT cells, following injection of α-GalCer pulsed, but not unpulsed DCs (FIG. 7A).

In some embodiments, the administration of mature α-galcer-pulsed DC's as exemplified herein, provide antigen-specific responses to antigens found in vivo, administered significantly prior (CMV) or following (flu) DC administration, without a need for conjoint administration.

In one embodiment, the NK T cell populations of this invention, or expanded via the methods of this invention, provide ultimately for antigen specific responses.

In one embodiment, the term "antigen specific" refers to a property of the population such that supply of a particular antigen, or in another embodiment, a fragment of the antigen, results, in one embodiment, in specific cell proliferation, when presented the antigen.

In one embodiment, NKT expansion is stimulated via contact with α-GalCer displayed in the context of CD1, on a mature DC. According to this aspect, and in one embodiment, expanded NKT cells elaborate cytokines, which in turn activate APCs, which present the antigen to appropriate effector T cells. In one embodiment NKT cell activation of APC results in enhanced costimulatory molecule expression, or in another embodiment, enhanced translocation of MHC from intracellular pools, or in another embodiment, enhanced processing of antigens for presentation. It is to be understood that any means whereby antigen-specific T cell responses are obtained, following NKT cell expansion due to α-GalCer-pulsed DC administration, is to be considered as part of this invention.

In one embodiment, according to this aspect of the invention, such methods are particularly applicable in subjects who are immunosuppressed, which may be a result of, in one embodiment, cancer therapy, or in another embodiment, infection with a virus, or in another embodiment, anti-psychotic therapy, or any cause for which a subject is rendered immunocompromised, due to, in some embodiments, an agent which the subject is being administered, or an agent to which the subject is exposed.

According to this aspect, and in one embodiment, the methods of this invention may allow for increased numbers of NKT cells which activate the immune system sufficiently to compensate, at least in part, for the immunocompromise in the subject. In one embodiment, as described herein, NKT cells which are expanded repeatedly may be pooled and frozen, and provided once "concentrated" as such, to enable concentrated administration of the NKT cells to a subject.

In one embodiment, the methods of the present invention are utilized, to stimulate or enhance an immune response to an infection, or in another embodiment, to bias an existing immune response, such as, for example, in circumstances wherein eliciting a "Th1" response is beneficial in a subject, wherein the subject has a disease where a so-called "Th2" type response has developed, or, in another embodiment, the reverse. According to this aspect, and in one embodiment, the methods of this invention, may allow for a shift toward a Th1 type response, or Th2 type response, as needed, in response to the cytokine profile produced following administration of the NK T cells, or dendritic cells, as described.

In one embodiment, the term "Th2 type response" refers to a pattern of cytokine expression, elicited by T Helper cells as part of the adaptive immune response, which support the development of a robust antibody response. Th2 type responses are beneficial in helminth infections in a subject, for example. Typically Th2 type responses are recognized by the production of interleukin-4 or interleukin 10, for example.

In one embodiment, the term "Th1 type response" refers to a pattern of cytokine expression, elicited by T Helper cells as part of the adaptive immune response, which support the development of robust cell-mediated immunity. Typically Th1 type responses are beneficial in intracellular infections in a subject, for example. Typically Th1 type responses are recognized by the production of interleukin-2 or interferon γ, for example.

In one embodiment, the methods may be utilized to bias a Th1 type response that has developed, when Th2 type responses provide a more beneficial outcome to a subject, where introduction of the NK T cells, vaccines or compositions of the present invention provides a shift to the more beneficial cytokine profile.

In one embodiment, the methods may be utilized to bias a Th2 type response that has developed, when Th1 type responses provide a more beneficial outcome to a subject, where introduction of the NK T cells, vaccines or compositions of the present invention provides a shift to the more beneficial cytokine profile.

One example would be in leprosy, where the NK T cells, vaccines or compositions of the present invention stimulates a Th1 cytokine shift, resulting in tuberculoid leprosy, as opposed to lepromatous leprosy, a much more severe form of the disease, associated with Th2 type responses. Another example may be where a Th1 response is initiated, and persists in the subject, such as for example, responses to the egg antigen is schistosomiasis, which are not beneficial to the subject, wherein bias to a Th2 response limits granlomatous responses which, in this case, result in tissue necrosis.

In another embodiment, the NK T cells of this invention, and obtained via the methods of this invention, may be a part of a vaccine or composition. Such vaccines and/or compositions may be used in any applicable method of this invention, and represents an embodiment thereof.

In one embodiment, the biasing of the immune response may be accomplished by administering α-GalCer-pulsed DCs, NK T cells and in combination with an antigen, an APC, cytokines, growth factors and other adjuvants.

For example, in one embodiment, the methods of this invention for stimulating, inhibiting, suppressing or modulating an immune response in a subject, which comprise contacting an NKT cell in a subject with α-GalCer-pulsed DCs, may also comprise contacting the NKT cell with a composition, or in another embodiment, a vaccine comprising the same. The composition and/or vaccine may further comprise additional antigens, cytokines, growth factors, adjuvants, an APC, or any combination thereof.

It will be appreciated by one skilled in the art that such methods, compositions, and vaccines may provide an antigen which is preferentially expressed in a tissue, against which an immune response is desired, such as, for example, neoplastic or preneoplastic tissue, or in another embodiment, infected tissue. In another embodiment, the cytokine milieu may be sufficient to stimulate an immune response which had been minimal or anergized, or suppressed. In another embodiment, the APCs which are genetically engineered to express a costimulatory molecule, and efficiently present a desired antigen, enhancing an immune response, or in another embodiment, to prevent or reduce anergy.

In some embodiments, the immune response may be enhanced or stimulated, in subjects, without additional supply of an antigen, such as exemplified hereinbelow, in the case of the generation of interferon-γ producing T cells to CMV. In some embodiments, immunity is stimulated via persistent antigen within a subject presented to T cells in the subject, as a consequence of NKT cell administration.

In other embodiments, the immune response may be enhanced or stimulated in subjects, via the additional supply of an antigen, a vaccine, and immunogenic composition, etc., such as exemplified hereinbelow, in the generation of Flu-MP specific memory T cells observed following concurrent injection of an influenza vaccine and α-GalCer-pulsed DCs.

In some embodiments, the immune response is directed against an antigen unrelated to that displayed on the α-GalCer-pulsed DCs, but as a result of immune system activation as a whole, following exposure to the DCs. In one embodiment, immune responses to antigens which persist in the subject are stimulated, or in another embodiment, vaccines co-administered, or administered within a small time frame, either prior to or following administration of the α-GalCer-pulsed DCs, is stimulated.

It is to be understood that any use of the α-GalCer-pulsed DCs and/or NKT cells, vaccines or compositions of the present invention for methods of enhancing immunogenicity, such as, for example, for purposes of immunizing a subject to prevent disease, and/or ameliorate disease, and/or alter disease progression are to be considered as part of this invention.

Examples of infectious virus to which stimulation of a protective immune response is desirable, which may be accomplished via the methods of this invention, or utilizing the NK T cells, vaccines or compositions of the present invention include: Retroviridae (e.g., human immunodeficiency viruses, such as HIV-1 (also referred to as HTLV-III, LAV or HTLV-III/LAV, or HIV-III; and other isolates, such as HIV-LP; Picornaviridae (e.g., polio viruses, hepatitis A virus; enteroviruses, human coxsackie viruses, rhinoviruses, echoviruses); Calciviridae (e.g., strains that cause gastroenteritis); Togaviridae (e.g., equine encephalitis viruses, rubella viruses); Flaviridae (e.g., dengue viruses, encephalitis viruses, yellow fever viruses); Coronaviridae (e.g., coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g. influenza viruses); Bungaviridae (e.g., Hantaan viruses, bunga viruses, phleboviruses and Nairo viruses); Arena viridae (hemorrhagic fever viruses); Reoviridae (erg., reoviruses, orbiviurses and rotaviruses); Bimaviridae; Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes viruses'); Poxviridae (variola viruses, vaccinia viruses, pox viruses); and Iridoviridae (e.g. African swine fever virus); and unclassified viruses (e.g., the etiological agents of *Spongiform encephalopathies*, the agent of delta hepatities (thought to be a defective satellite of hepatitis B virus), the agents of non-A, non-B hepatitis (class 1=internally transmitted; class 2=parenterally transmitted (i.e., Hepatitis C); Norwalk and related viruses, and astroviruses).

Examples of infectious bacteria to which stimulation of a protective immune response is desirable, which may be accomplished via the methods of this invention, or utilizing the NK T cells, vaccines or compositions of the present invention include: *Helicobacter pyloris, Borellia burgdorferi, Legionella pneumophilia, Mycobacteria* sps (e.g. *M. tuber-* culosis, *M. avium, M. intracellulare, M. kansaii, M. gordonae*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (*viridans* group), *Streptococcus faecalis, Streptococcus bovis, Streptococcus* (*anaerobic* sps.), *Streptococcus pneumoniae*, pathogenic *Campylobacter* sp., *Enterococcus* sp., *Chlamidia* sp., *Haemophilus influenzae, Bacillus antracis, corynebacterium diphtheriae, corynebacterium* sp., *Erysipelothrix rhusiopathiae, Clostridium perfringers, Clostridium tetani, Enterobacter aerogenes, Klebsiella pneumoniae, Pasturella multocida, Bacteroides* sp., *Fusobacterium nucleatum, Streptobacillus moniliformis, Treponema pallidium, Treponema pertenue, Leptospira, Actinomyces israelli* and *Francisella tularensis.*

Examples of infectious fungi to which stimulation of a protective immune response is desirable, which may be accomplished via the methods of this invention, or utilizing the NK T cells, vaccines or compositions of the present invention include: *Cryptococcus neoformans, Histoplasma capsulatum, Coccidioides immitis, Blastomyces dermatitidis, Chlamydia trachomatis, Candida albicans*. Other infectious organisms (i.e., protists) include: *Plasmodium* sp., *Leishmania* sp., *Schistosoma* sp. and *Toxoplasma* sp.

In one embodiment, the infection is a latent infection.

In one embodiment, the subject being treated via a method of this invention has a precancerous precursor, and/or is at an elevated risk for cancer. Such elements are well known in the art, and may comprise inappropriate expression of a given surface marker or oncoprotein, the presence of hyperplastic cells, or the subject may have at least one family member afflicted with a given cancer, or have a lifestyle associated with enhanced risk for the incidence of cancer, such as, for example, exposure to radiation, certain viral infections, smoking tobacco products, and others, as will be appreciated by one skilled in the art.

In one embodiment, the NK T cells can be used to modulate an immune response, in a disease-specific manner. It is to be understood that any immune response, wherein it is desired to enhance cytokine production, or elicit a particular cytokine profile, including interferon-γ, interleukin-2 and/or interleukin-4, the α-GalCer pulsed DCs and/or NK T cells of this invention may be thus utilized, and represent embodiments of this invention.

In another embodiment, the methods of this invention may further comprise the step of culturing previously expanded and isolated NKT cells with additional dendritic cells, and α-GalCer, for a period of time resulting in further NK T cell expansion, cytokine production, or a combination thereof.

In one embodiment, DC mediated human NKT activation, via the methods of this invention may be utilized for downstream DC, or other APC activation and, in another embodiment, for enhanced memory T cell function in vivo. In one embodiment, the defects reported in DC maturation, which underlie immune paralysis in cancer and HIV infection, for example, are treated with the methods, cells, vaccines and/or compositions of this invention. In one embodiment, NKT cell mediated DC activation in vivo, specifically alleviates cancer-associated immune paresis. In another embodiment, enhancement of T cell memory via the methods, cells, vaccines and/or compositions of this invention find particular application in subjects with persistent viral infections such as HIV or hepatitis. In another embodiment, the methods of this invention may comprise the combination therapy of the cells, vaccines, and/or compositions of this invention with other vaccines that target T cells, particularly against tumors and chronic viral infections.

In one embodiment, cells for administration to a subject in this invention may be provided in a composition. These compositions may, in one embodiment, be administered parenterally or intravenously. The compositions for administration may be, in one embodiment, sterile solutions, or in other embodiments, aqueous or non-aqueous, suspensions or emulsions. In one embodiment, the compositions may comprise propylene glycol, polyethylene glycol, injectable organic esters, for example ethyl oleate, or cyclodextrins. In another embodiment, compositions may also comprise wetting, emulsifying and/or dispersing agents. In another embodiment, the compositions may also comprise sterile water or any other sterile injectable medium. In another embodiment, the compositions may comprise adjuvants, which are well known to a person skilled in the art (for example, vitamin C, antioxidant agents, etc.) for some of the methods as described herein, wherein stimulation of an immune response is desired, as described further hereinbelow.

In one embodiment, the compounds, cells, vaccines or compositions of this invention may be administered to a subject via injection. In one embodiment, injection may be via any means known in the art, and may include, for example, intra-lymphoidal, or subcutaneous injection.

In one embodiment, antigen, which includes, inter-alia, α-GalCer, or other antigens for use as described in the methods of this invention, may be delivered to dendritic cells in vivo in the steady state, which, in another embodiment, leads to expansion of disease specific T cells. Antigen delivery in the steady state can be accomplished, in one embodiment, as described (Bonifaz, et al. (2002) Journal of Experimental Medicine 196: 1627-1638; Manavalan et al. (2003) Transpl Immunol. 11: 245-58).

In another embodiment, the cells administered as part of the methods of this invention may be administered to a recipient contemporaneously with treatment for a particular disease, such as, for example, contemporaneous with standard anti-cancer therapy, to serve as adjunct treatment for a given cancer. In another embodiment, the cells may be administered prior to the administration of the other treatment.

It is to be understood that the modulation of any immune response, via the use of the NKT cell populations, vaccines or compositions of this invention are to be considered as part of this invention, and an embodiment thereof.

In another embodiment, the α-GalCer-pulsed DCs and/or NK T cell populations of, and/or for use in the methods of this invention may be isolated, culture-expanded, or otherwise manipulated, as will be understood by one skilled in the art. In one embodiment, the α-GalCer-pulsed DCs and/or NK T cell populations as derived by the methods of this invention, may be further engineered to express substances of interest. In one embodiment, the α-GalCer-pulsed DCs and/or NK T cell populations may be engineered to express particular adhesion molecules, or other targeting molecules, which, when the cells are provided to a subject, facilitate targeting of the cells to a site of interest. For example, when NK T cell activity is desired to modulate an immune response at a mucosal surface, the isolated NK T cell populations of this invention may be further engineeered to express the $\alpha_e\beta_7$ adhesion molecule, which has been shown to play a role in mucosal homing. The cells can be engineered to express other targeting molecules, such as, for example, an antibody specific for a protein expressed at a particular site in a tissue, or, in another embodiment, expressed on a particular cell located at a site of interest, etc. In another embodiment, the NK T cells and dendritic cells for administration in this invention may be engineered to express chemokine receptors, in addition to adhesion molecules, and in another embodiment, expression of the same may serve to attract the cells to secondary lymphoid organs for priming. In another embodiment, targeting of cells to these sites may be accomplished via injecting the cells directly to secondary lympoid organs through intralymphatic or intranodal injection.

Numerous methods are well known in the art for engineering the cells, and may comprise the use of a vector, or naked DNA, wherein a nucleic acid coding for the targeting molecule of interest is introduced via any number of methods well described.

A nucleic acid sequence of interest may be subcloned within a particular vector, depending upon the desired method of introduction of the sequence within cells. Once the nucleic acid segment is subcloned into a particular vector it thereby becomes a recombinant vector. Polynucleotide segments encoding sequences of interest can be ligated into commercially available expression vector systems suitable for transducing/transforming mammalian cells and for directing the expression of recombinant products within the transduced cells. It will be appreciated that such commercially available vector systems can easily be modified via commonly used recombinant techniques in order to replace, duplicate or mutate existing promoter or enhancer sequences and/or introduce any additional polynucleotide sequences such as for example, sequences encoding additional selection markers or sequences encoding reporter polypeptides.

There are a number of techniques known in the art for introducing the above described recombinant vectors into cells, such as, but not limited to: direct DNA uptake techniques, and virus, plasmid, linear DNA or liposome mediated transduction, receptor-mediated uptake and magnetoporation methods employing calcium-phosphate mediated and DEAE-dextran mediated methods of introduction, electroporation, liposome-mediated transfection, direct injection, and receptor-mediated uptake (for further detail see, for example, "Methods in Enzymology" Vol. 1-317, Academic Press, Current Protocols in Molecular Biology, Ausubel F. M. et al. (eds.) Greene Publishing Associates, (1989) and in Molecular Cloning: A Laboratory Manual, 2nd Edition, Sambrook et al. Cold Spring Harbor Laboratory Press, (1989), or other standard laboratory manuals). Bombardment with nucleic acid coated particles is also envisaged.

The efficacy of a particular expression vector system and method of introducing nucleic acid into a cell can be assessed by standard approaches routinely used in the art. For example, DNA introduced into a cell can be detected by a filter hybridization technique (e.g., Southern blotting) and RNA produced by transcription of introduced DNA can be detected, for example, by Northern blotting, RNase protection or reverse transcriptase-polymerase chain reaction (RT-PCR). The gene product can be detected by an appropriate assay, for example by immunological detection of a produced protein, such as with a specific antibody, or by a functional assay to detect a functional activity of the gene product, such as an enzymatic assay. If the gene product of interest to be expressed by a cell is not readily assayable, an expression system can first be optimized using a reporter gene linked to the regulatory elements and vector to be used. The reporter gene encodes a gene product, which is easily detectable and, thus, can be used to evaluate efficacy of the system. Standard reporter genes used in the art include genes encoding β-galactosidase, chloramphenicol acetyl transferase, luciferase and human growth hormone, or any of the marker proteins listed herein.

In another embodiment, this invention provides a method for delaying onset, reducing incidence, suppressing or reducing the severity of neoplasia in a subject, comprising the steps of:
a. contacting mature dendritic cells isolated from a subject having or predisposed to having neoplasia with α-galactosyl ceramide; and
b. contacting the cells in (a) with an NKT cell population in a subject;

whereby said NKT cells undergo expansion to yield at least 100 NKT cells per $1 \times 10^6$ lymphocytes in the peripheral blood of said subject and said NKT cells participate in an antineoplastic response in said subject.

In one embodiment, according to this aspect of the invention, the subject is afflicted with, or is predisposed to neoplasia, which in another embodiment, a carcinoma or myeloma.

In one embodiment, the subject has preneoplastic or hyperplastic cells or tissue. In one embodiment, the method further comprises the step of reimplanting the NKT cells, dendritic cells or a combination thereof in said subject. In one embodiment, the dendritic cells are autologous with respect to said NKT cells.

It is to be understood that any of the embodiments listed herein as regards to the cells, their isolation, their expansion, modes of administration, compounds which may be administered concurrently, compositions comprising the cells, etc., are to be considered as applicable for each method of this invention and an embodiment thereof.

As described herein, the methods as described herein facilitate NKT cell expansion, immune system activation, and antigen-specific responses, or general immune activation, in another embodiment. In one embodiment, the latter application is useful in treating subjects with neoplasia, and/or subjects undergoing radiation/chemotherapy for the neoplasia, where the subject is immunosuppressed. According to this aspect of the invention, and in one embodiment, the methods as described prevent or palliate patient morbidity or mortality associated with immunosuppression brought about as a byproduct of treatment of the neoplasia.

In one embodiment, the immune response inhibits disease progression in the subject, or in another embodiment, the immune response inhibits or prevents neoplastic transformation in the subject.

In another embodiment, the method further comprises administering an antigen to the subject, which in one embodiment is a protein or peptide, which in another embodiment is preferentially expressed or expressed in greater concentration in neoplastic cells or tissue.

In one embodiment, inhibition or prevention of neoplastic transformation according to the methods of this invention may be effected via the use of tumor specific antigens, in addition to the cells, and as part of the vaccines and/or compositions of this invention. In one embodiment, a tumor specific antigen may be, for example, mutated proteins which are expressed as a result of a neoplastic, or preneoplastic events. In one embodiment, the antigen is a molecule associated with malignant tumor cells, such as, for example altered ras. Non-limiting examples of tumors for which tumor specific antigens have been identified include melanoma, B cell lymphoma, uterine or cervical cancer.

In one embodiment, a melanoma antigen such as the human melanoma specific antigen gp75 antigen may be used, or, in another embodiment, in cervical cancer, papilloma virus antigens may be used for the methods of this invention. Tumor specific idiotypic protein derived from B cell lymphomas, or in another embodiment, antigenic peptide or protein is derived from the Epstein-Bass virus, which causes lymphomas may be used, as well.

In another embodiment, the antigenic peptide or protein is derived from HER2/neu or chorio-embryonic antigen (CEA) for suppression/inhibition of cancers of the breast, ovary, pancreas, colon, prostate, and lung, which express these antigens. Similarly, mucin-type antigens such as MUC-1 can be used against various carcinomas; the MAGE, BAGE, and Mart-1 antigens can be used against melanomas. In one embodiment, the methods may be tailored to a specific cancer patient, such that the choice of antigenic peptide or protein is based on which antigen(s) are expressed in the patient's cancer cells, which may be predetermined by, in other embodiments, surgical biopsy or blood cell sample followed by immunohistochemistry.

It is to be understood that any disease, disorder or condition, whereby such disease, disorder or condition may be positively affected by the methods and/or cells, vaccines or compositions of this invention, is to be considered as part of this invention. In another embodiment, this invention provides an in vivo-expanded NKT cell population isolated from a subject, wherein said population is characterized by $CD4^+$, $CD8^+$ or $CD4^-CD8^-$ surface expression and wherein said population is at a concentration of at least 100 NKT cells per $1 \times 10^6$ lymphocytes in the peripheral blood of said subject. In one embodiment, the isolated, in vivo-expanded NKT cell population is at a concentration ranging from at least $100-1 \times 10^4$ per $1 \times 10^6$ lymphocytes in said subject, or in another embodiment, the isolated, in vivo-expanded NKT cell population is at a concentration ranging from at least $5 \times 10^2 - 1 \times 10^3$ per $1 \times 10^6$ lymphocytes, or in another embodiment, at least $1 \times 10^3 - 5 \times 10^3$ or in another embodiment, at least $5 \times 10^3 - 1 \times 10^4$ lymphocytes in said subject.

In some embodiments, this invention provides for NKT cell expansion, which occurs more readily, and for a longer period of time, in vivo, than that obtained in vitro, as a function of the use of dendritic cells which are mature in vivo, as compared to in vitro use of immature dendritic cells. In some embodiments, NKT cell expansion in vivo occurs in immunosuppressed or immunocompromised subjects, with expansion increasing over baseline, or being prolonged over a long course of time, or a combination thereof.

The following non-limiting examples may help to illustrate some embodiments of the invention.

EXAMPLES

Materials and Methods

Study Design and Eligibility:

The study design was a single arm open label trial to test the feasibility and tolerability of injection of unpulsed and KRN-7000 pulsed DCs in patients with advanced cancer (FIG. 1). Patients with relapsed or persistent myeloma after initial therapy, metastatic renal cell cancer, unresectable or metastatic hepatocellular cancer, or metastatic cancer of any histologic type that had failed prior standard therapy were eligible. Other eligibility criteria were: Eastern Cooperative Oncology Group (ECOG) performance score of 0-2, age>18 years, and adequate organ function (hemoglobin>8 g/di, WBC>3000/□l, serum transaminases<4× upper normal limits, and serum bilirubin<3 mg/dl. Patients with active or chronic infections, known clinical autoimmune disease, Gaucher's disease, pregnant or lactating females were excluded. All patients signed an informed consent approved by the Rockefeller University Institutional Review Board, and the study was conducted under an Investigational New Drug application approved by the Food and Drug Administration.

Treatment and Monitoring Schema:

After screening and registration, patients underwent a 2-3 hour steady state leukapheresis for the collection of DC progenitors. All patients received an initial intravenous injection of 5 million unpulsed monocyte derived mature DCs, followed at monthly intervals by two additional injections of mature DCs pulsed with □-galactosyl ceramide (□-GalCer; KRN-7000). Unpulsed DCs were injected as a control due to the possibility that mature DCs alone might stimulate NKT cells in vivo (45). After each injection, patients were observed overnight at the Rockefeller University General Clinical Research Center (GCRC). Patients were evaluated at 4 and 7 days after each injection; 30 days after the last injection, and every 3 months thereafter, until removal from the study. Complete blood count and serum chemistries including liver function tests were monitored at baseline, 1 day, 7 days and 1 month after each injection. Patients were also monitored for the development of rheumatoid factor or anti-nuclear antibodies.

Generation of DCs:

Dendritic cells (DCs) were generated from blood monocytes using a protocol adapted from Thurner et al, in a dedicated facility under good tissue practices (GTP) guidelines (Thurner, B., et al. 1999. J Immunol Methods 223:1-15). Briefly, mononuclear cells were isolated from leukapheresis specimens using Ficoll Hypaque density gradient centrifugation and cryopreserved in aliquots. For generating DCs, the mononuclear cells were thawed and allowed to adhere in tissue culture plates. Adherent monocytes were then cultured in RPMI1640 (Biowhittaker, Walkersville, Md.) supplemented with 1% autologous plasma, in the presence of 20 ng/ml GM-CSF (Immunex, Seattle, Wash.) and 20 ng/ml IL-4 (Cell Genix, Freiberg, Germany). The cultures were supplemented with cytokines on days 1, 3 and 5 of culture. On day 5, immature DCs were transferred to fresh 6 well plates, and induced to mature using an inflammatory cytokine cocktail consisting of IL-1β (10 ng/ml; Cell Genix), IL-6 (1000 U/ml; Cell Genix), TNF-= ng/ml; Cell Genix), and $PGE_2$ (1 μg/ml; Pharmacia). For KRN-7000 loading, DCs were pulsed with 100 ng/ml of KRN-7000 at the time of DC maturation. The DCs were harvested for injection about 20 hours after the induction of maturation, and resonstituted in 5% autologous plasma in normal saline at 1 million DCs/ml, before intravenous injection. Release criteria for DCs were viability>80%, purity>50%, maturity (expressed as % CD83+ cells)>60%, negative gram stain, endotoxin and mycoplasma PCR, and negative in process cultures from samples sent 48 hours before release. Post release tests included negative extended sterility cultures, and mycoplasma PCR. DC preparations were also monitored for the ability to stimulate allogeneic mixed lymphocyte reactions. Effective loading of the final product with α-GalCer was monitored by testing the ability of these DCs to expand NKT cells in culture, without further ex vivo loading. All products met all release criteria and post release testing, and the DCs had a typical phenotype of CD14−, HLA-DR+, and CD83+ cells.

Immunologic Monitoring:

Immune monitoring was predominantly carried out using blood samples. In all patients, at least three baseline samples were obtained prior to the first injection in order to establish a baseline. Follow up samples for immune monitoring were obtained at 6 hours, 24 hours, 4 days, 7 days, and 1 month after each DC injection, and every 3 months after the last injection. When possible, samples of bone marrow aspirates in myeloma patients were utilized to assess the changes in NKT cells in the tumor bed before and after vaccination.

Number and Subsets of NKT Cells:

The numbers of NKT cells in freshly isolated blood or bone marrow mononuclear cells were quantified by multi-parameter flow cytometry, based on the expression of invariant T cell receptor (Vα24/Vβ11) both on the cell surface as well as intracellularly after permeabilisation using saponin, and binding to CD1d dimer (DimerX, BD Biosciences) loaded with α-GalCer using the manufacturer's recommendations. At least $2 \times 10^5$ lymphocyte gated events were acquired to allow reliable estimation of NKT cells. Subsets of expanded NKT cells were monitored based on the expression of CD4 or CD8 on invariant T cell receptor positive cells.

Functional Studies on NKT Cells:

Functional aspects of NKT cells were assayed based on cytokine production and proliferation in response to α-GalCer. Cytokine production was measured both in fresh PBMCs and after in vitro expansion using α-GalCer loaded DCs, and analyzed by Elispot, intracellular cytokine flow cytometry, quantitative RT-PCR by TaqMAN, and multiplex cytokine analysis.

Stimulation of NKT Cells in Culture:

To asses the ability of NKT cells to proliferate in culture, pre and post immunization PBMCs were thawed together and cultured in the presence of autologous α-GalCer pulsed monocyte derived mature DCs (on unpulsed DCs as a control), at DC:PBMC ratio of 1:20 in the presence of 50 U/ml of IL-2 (Chiron), as described (19, 22). Expansion of NKT cells was monitored by quantifying Vα24+/Vβ11+ or CD1d-α-GalCer DimerX binding NKT cells by flow cytometry.

Elispot Assay for Interferon-γ Producing T/NKT Cells:

To detect interferon-γ producing NKT cells, freshly isolated PBMCs ($5 \times 10^5$ cells/well) were cultured overnight in the presence of 100 ng/ml α-GalCer in Elispot plates precoated with anti-interferon-γ antibody (Mabtech, Stockholm, Sweden), as described (Dhodapkar, M. V., et al. 2003. J. Exp. Med. 197:1667-1676). For detecting influenza specific T cells, PBMCs were infected with influenza (MOI=2) before plating in the Elispot assay. Staphylococcal Enterotoxin A (50 ng/ml; SEA) was used as a positive control. In HLA A2+ patients, antigen specific T cells against A2 restricted peptides from influenza matrix protein and CMV pp65 were also monitored using this assay, as described (Dhodapkar, M. V., and Steinman, R. M. 2002. Blood 100:174-177).

Intracellular Cytokine Detection by Flow Cytometry:

For the detection of intracellular cytokine secretion (ICS), freshly isolated PBMCs were cultured overnight with 100 ng/ml α-GalCer in the presence of anti-CD28 (3 □g/ml; BD Biosciences), or anti-CD28 alone as a control in the presence of 0.7 μg/ml Golgi Stop (from Cytofix/Cytoperm Plus kit from BD Biosciences). Stimulation with PMA (50 ng/ml) and ionomycin (1 μM) was used as positive control. The presence of interferon-γ producing Vα24+/Vβ11+ cells was quantified by flow cytometry, as described (Dhodapkar, M. V., et al. 2003. J. Exp. Med. 197:1667-1676). For the detection of intracellular cytokine production by expanded NKT cells (after 1 week culture with DCs as described above; recall ICS), these cells were restimulated overnight with unpulsed or α-GalCer loaded DCs (DC: responder ratio 1:10), prior to staining and analysis, as described.

TaqMan RT-PCR Quantitaton of mRNA

Analysis of α-GalCer reactive cytokine production in the Elispot and ICS assays was limited to interferon-γ. Therefore, we utilized cytokine multiplex analysis (CMA) and TaqMan RT-PCR to assay the production of alternate cytokines in these cultures. For the TaqMan analysis, PBMCs were cultured with α-GalCer as described earlier. For some assays, pre and post immunization samples expanded with DCs were restimulated with unpulsed or α-GalCer loaded DCs (DC: responder ratio of 1:10) for 8 hours. Stimulated cells were pelleted and total RNA was isolated using the QIAGEN RNeasy kit. The primers and probes for interferon-γ, IL-4, IL-10 and IL-13 were purchased from Applied Biosystems/Perkin Elmer. RT-PCR reactions were performed in duplicate samples according to the manufacturer's directions (EZ PCR Core Reagents; TaqMan and Applied Biosystems), using an Applied Biosystems PRISM 7700 Thermal cycler, as described (Lee, E., et al. 2004. J Exp Med 199:125-130). mRNA levels for a housekeeping gene GAPDH were used to normalize each gene from each sample.

Cytokine Mukiplex Analysis:

Serum was analyzed for 20 cytokines and chemokines using the Protein Multiplex Immunoassay kit (Biosource International) as per manufacturer's protocol. Briefly, Biosource's Multiplex beads were vortexed and sonicated for 30 sec. and 25 μl was added to each well and washed 2× with wash buffer. The samples were diluted 1:2 with assay diluent and loaded onto a Millipore Multiscreen BV 96-well filter plate with 50 μl of incubation buffer previously added to each well. Serial dilutions of cytokine standards were prepared in parallel and added to the plate. Samples were then incubated on a plate shaker at 600 rpm in the dark at room temperature for 2 hours. The plate was applied to a Millipore Multiscreen Vacuum Manifold and washed twice with 200 μl of wash buffer. 100 μl of biotinylated Anti-Human Multi-Cytokine Reporter was added to each well. The plate was incubated on a plate shaker at 600 rpm in the dark at room temperature for 1 hour. The plate was applied to a Millipore Multiscreen Vacuum Manifold and washed twice with 200 μl of wash buffer. Streptavidin-Phycoerythrin was diluted 1:10 in wash buffer, and then 100 μl was added directly to each well. The plate was incubated on a plate shaker at 600 rpm in the dark at room temperature for 30 minutes. The plate was then applied to the vacuum manifold, washed twice, and each well resuspended in 100 μl wash buffer and shaken for 1 minute. The assay plate was then transferred to the Bio-Plex Luminex 100 XYP instrument for analysis. Cytokine concentrations were calculated using Bio-Plex Manager 3.0 software with a 5 parameter curve fitting algorithm applied for standard curve calculations.

Analysis of NK Cell Subsets and Activation:

The numbers of NK cells and their subsets (CD16neg CD56hi; CD16pos CD56lo) in blood mononuclear cells before and after vaccination were monitored by flow cytometry. The activation status of NK cells was monitored based on the expression of CD69 and natural cytotoxicity receptors (p30, p44 and p46).

Analysis of Antigen Specific T Cell Responses:

Influenza virus specific T cells were monitored by Elispot and intracellular cytokine staining, as described earlier (Dhodapkar, M. V., et al. 2003. J. Exp. Med. 197:1667-1676). In HLA-A2+ patients, T cell responses to A2 restricted epitopes derived from influenza matrix protein and CMVpp65 were monitored by Elispot in fresh PBMCs. Antigen specific T cells against these epitopes were also quantified by MHC-tetramers, as described (Dhodapkar, M. V., et al. 1999. J. Clin. Invest. 104:173-180). To assess the ability of memory T cells to proliferate in culture, pre and post immunization samples were thawed and cultured with peptide pulsed DCs as described. After 1 week of culture, antigen specific CD8+ T cells were quantified using MHC tetramers.

Statistical Analysis:

Data from pre and post immunization assays were compared using the Student's T test, or Mann Whitney test. Significance was set at $p<0.05$.

Example 1

α-GalCer Loaded DCs Leads to Increased Numbers of NKT Cells in Humans

Four human subjects were evaluated for the course of the experiment, which consisted of 3 vaccines (FIG. 1). The patient characteristics are shown in Table 1.

noted to have an increase in activated partial thromboplastin time post vaccination, thought to be secondary to an inhibitor. There was no clinical evidence of autoimmunity or hepatic toxicity in any patient.

None of the patients had detectable circulating NKT cells at baseline, which was likely due to extensive prior therapy of the underlying malignancy. The injection of unpulsed DCs did not lead to an increase in NKT cells in any patient at any time point. In contrast, the injection of α-GalCer pulsed DCs led to more than a 100-fold increase in circulating NKT cells in all patients (FIG. 2A). This was detectable as an increase in cells positive for both invariant TCR and α-GalCer-CD1d dimer binding (FIG. 2B-D). NKT cells peaked at 7-30 days post vaccination and were already increased after the first injection of α-GalCer pulsed DCs in 3 of 4 patients. Importantly, the numbers of NKT cells stayed above baseline for more than 84 days in all patients, and were elevated above baseline for more than 6 months in two patients with longer follow up. There was a transient decline in circulating NKT

TABLE 1

Patient Characteristics

| Pt ID | Age | Sex | Diagnosis | Stage | Prior Therapy | Disease Status at | Disease at Study | Best Response | Duration on study | Current Status |
|---|---|---|---|---|---|---|---|---|---|---|
| K-1 | 62 | M | Myeloma | III | Chemotherapy, Stem Cell | Progressive | Urine M spike 3.3 | Urine M spike | 9 | Alive |
| K-2 | 41 | M | Myeloma | III | Chemotherapy, Stem Cell | Stable | Serum M spike 1.0 | Serum M spike | 10 | Alive |
| K-3 | 57 | M | Anal Ca | IV | Radiation, Chemotherap | Progressive | Metastases to liver, | None | 4 | Deceased |
| K- | 70 | M | Renal | IV | Surgery, | Progressi | Metastase | Stable | 8+ | Alive |

Each subject received prior extensive cancer therapy, and 3 of the 4 subjects had objective evidence of progressive disease at study entry. The characteristics of the DC preparations are shown in Table 2. All DC preparations met all release criteria and post release testing.

The DC injections were well tolerated in all patients with no greater than grade 2 injection related toxicity (Table 2).

cells on day 1 after DC injection. This decline was not due to TCR downregulation, because the number of intracellular TCR+ cells were also monitored and closely followed cell surface staining (data not shown). It should be noted that prior studies in mice showing TCR downregulation in NKT cells after injection of α-GalCer had monitored splenic but not blood NKT cells, as measured here. In one patient with

TABLE 2

Dendritic Cell Characteristics

| Pt ID | DC injection # | Dose ($10^6$) | Viability | Purity | Maturity (% CD83+) | Injection related Toxicity |
|---|---|---|---|---|---|---|
| K-1 | 1 (Unpulsed DCs) | 5 | 100 | 83 | 94 | Fever (grade 2) |
| K-1 | 2 (KRN-7000 pulsed | 5 | 99 | 83 | 94 | None |
| K-1 | 3 (KRN-7000 pulsed | 5 | 99 | 61 | 90 | None |
| K-2 | 1 (Unpulsed DCs) | 5 | 100 | 52 | 94 | None |
| K-2 | 2 (KRN-7000 pulsed | 5 | 98 | 58 | 83 | None |
| K-2 | 3 (KRN-7000 pulsed | 5 | 99 | 53 | 89 | None |
| K-3 | 1 (Unpulsed DCs) | 5 | 99 | 95 | 86 | None |
| K-3 | 2 (KRN-7000 pulsed | 5 | 96 | 92 | 66 | None |
| K-3 | 3 (KRN-7000 pulsed | 5 | 97 | 90 | 67 | None |
| K-4 | 1 (Unpulsed DCs) | 5 | 100 | 86 | 93 | None |
| K-4 | 2 (KRN-7000 pulsed | 5 | 99 | 80 | 93 | None |
| K-4 | 3 (KRN-7000 pulsed DCs) | 5 | 98 | 89 | 94 | ANA, RF positive; Increase in aPTT |

One patient developed rheumatoid factor and transient positive antinuclear antibody at follow up testing one month after the third injection. This patient was also incidentally myeloma, we looked for NKT cells in the marrow tumor bed both before and after DC vaccination, and we could demonstrate sustained expansion of invariant NKT cells there for more than 3 months post vaccination (FIG. 2E). Thus injection of α-GalCer loaded DCs led to a sustained increase in NKT cells in both blood as well as the tumor bed.

Example 2

Phenotype of Expanded NKT Cells

Recent studies have shown that the subset of cells binding to α-GalCer loaded CD1d tetramers can include both invariant TCR+ and invariant TCR− cells. In one study, many of the Vα24−, tetramer+ cells were Vβ11+, suggesting alternate Vα TCR usage by the CD1d multimer+ cells. The kinetics of increase in CD1d-glycolipid dimer+ and Vα24/Vβ11+ cells in all patients were closely matched (FIG. 2C-D). However, the numbers of dimer+Vαβ11+ cells generally exceeded the numbers of Vα24/Vβ11+ cells, or dimer+Vα24+ cells. Indeed, the expansion of dimer+Vα24− populations could also be demonstrated by flow cytometry (FIG. 2D). Therefore DC vaccination led to increases in both dimer+Vα24+ and dimer+Vα24− NKT cells in vivo, with similar kinetics.

Figure 3A:
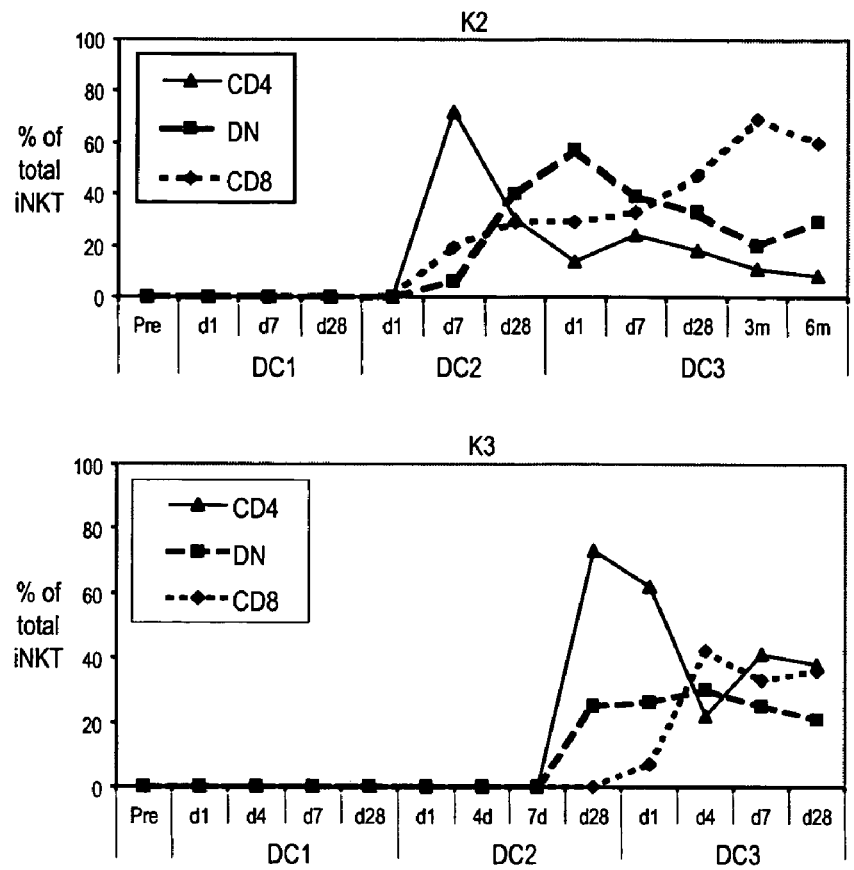
FIG. 3 demonstrates the kinetics of NKT subsets after the injection of α-GalCer pulsed DCs. (A) Proportion of CD4+, double negative or CD8+ subsets of NKT cells after α-GalCer/DC vaccination in two patients (K2 and K3), as analyzed by flow cytometry. (B) Representative FACS plots from a patient (K2), showing subsets of mobilized NKT cells, at early, mid or later time points, as shown in FIG. 3A. In the lower panel, numbers in the upper right quadrant are % of CD4+/double negative/CD8+, respectively of total NKT cells.
Figure 3B:
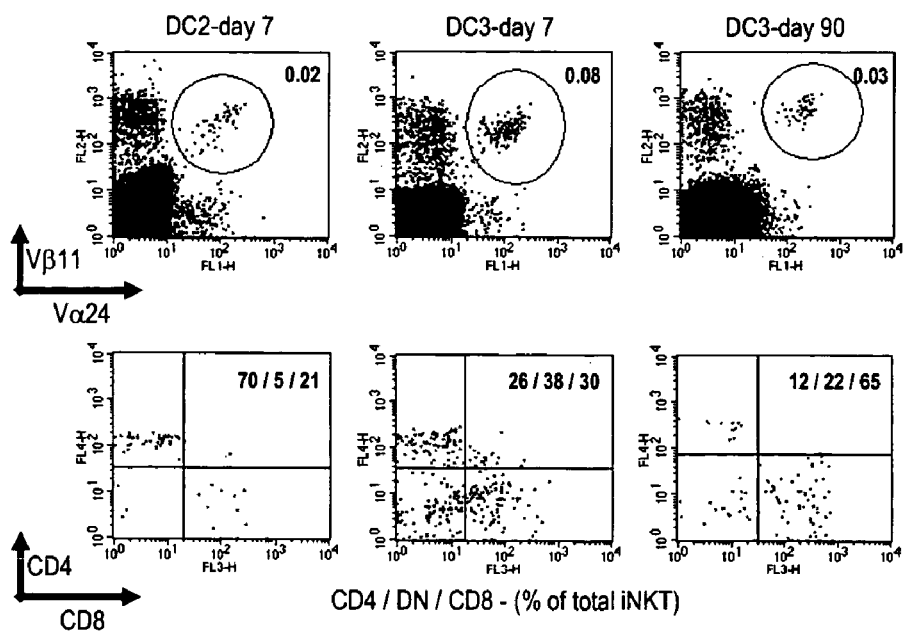

Recent studies have shown that human NKT cells consist of functionally distinct subsets based on the expression of CD4/CD8. In two patients with post vaccination frequency of more than $10^3$ NKT cells/$10^6$ PBMCs (K2, K3), the proportion of NKT subsets was analyzed by flow cytometry. In both patients, the phenotype of expanded invariant TCR+ cells was predominantly CD4+ at the early time points, but later time points, we noted an increase in double negative and CD8+ NKT cells (FIG. 3A-B). Thus, DC mediated mobilization of NKT cells in humans is associated with expansion of all three human NKT subsets in circulation, which may however have different kinetics of mobilization.

Example 3

Figure 4A:
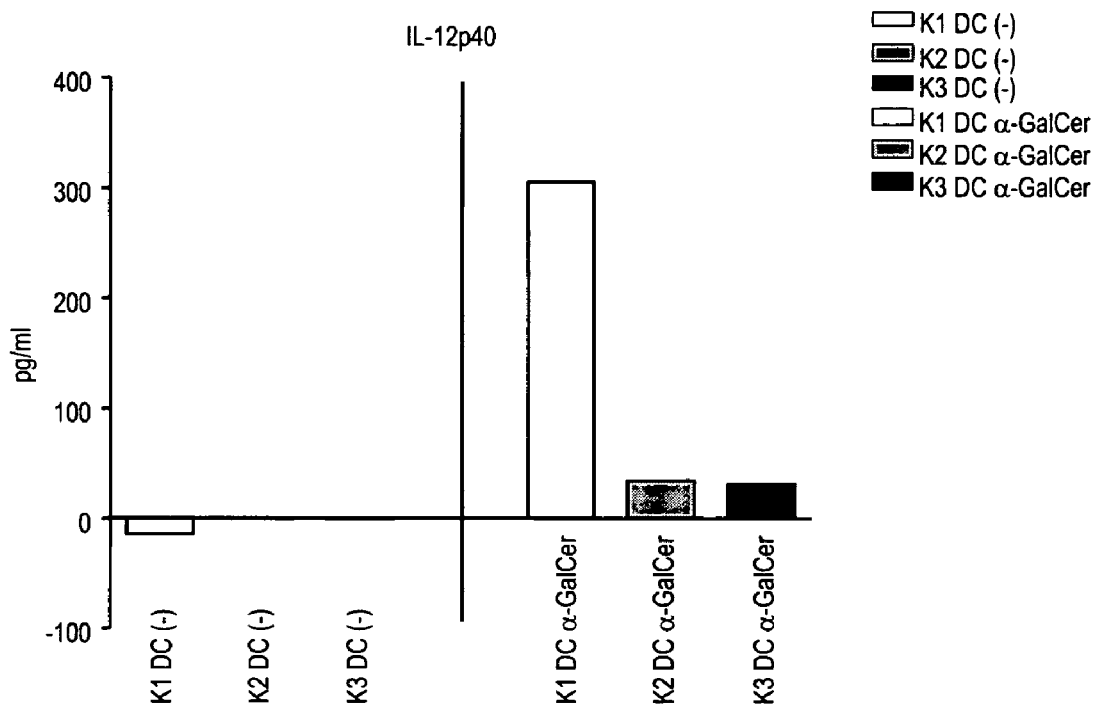
FIG. 4 demonstrates cytokine multiplex analysis. Increase or decrease in serum levels before and 24 hours after unpulsed (first Dc injection) or α-GalCer pulsed DC vaccine (3rd DC injection) were analyzed separately for each patient by Luminex. (A) Changes in serum IL-12p40. (B) Changes in serum IP-10. (C) Changes in serum MIP-1β.
Figure 4B:
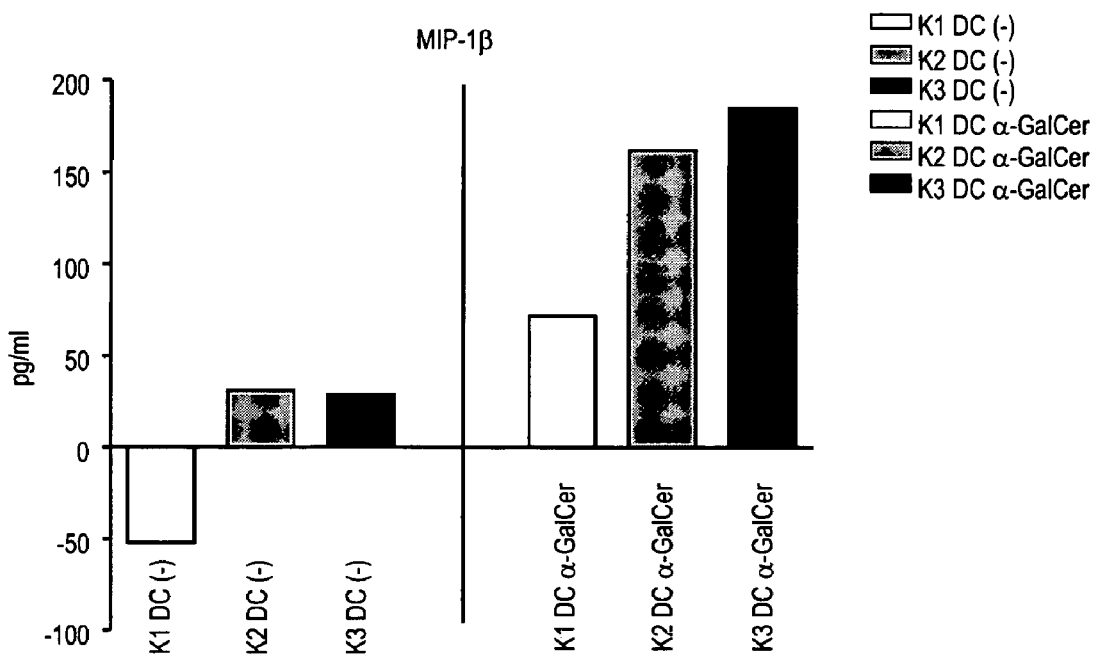

NKT Cell Cytokine Production

α-GalCer mediated NKT activation in vivo can lead to changes in serum cytokines in mice, however, changes in serum cytokines can also occur as a result of DC vaccination alone and changes in the underlying disease. In order to distinguish these effects from those specifically due to α-GalCer mediated activation, we analyzed paired serum samples before and 24 hr after each vaccine for 20 cytokines/chemokines using a cytokine multiplex method. Changes in the serum levels after α-GalCer pulsed DCs for each cytokine in each patient were then analyzed in the context of the changes after unpulsed DCs as a control. The sera from one patient (K4, who also developed ANA/RF positively post vaccine; Table 1) showed a high background from both baseline and post vaccine samples, consistent with autoimmune phenotype and were not analyzable by this method. The following cytokines were analyzed in this assay: IL-1β, IL-2, IL-4, IL-5, IL-6, IL-8, IL-10, IL-12 p40, IL-13, IL-15, IL-17, interferon-γ, TNF-α, GM-CSF, MIP-1α, MIP-1β, IP-10, MCP-1, eotaxin and RANTES. Of this panel, 3 cytokines IL-12 p40, IP-10 and MIP-1β consistently showed a statistically significant increase after injection of α-GalCer loaded DCs ($3^{rd}$ vaccine), but not unpulsed DCs (first vaccine) in all subjects tested (FIG. 4A-C). Similar findings were noted when first and second vaccines were compared (data not shown). This coupled with transient but α-GalCer-specific decline in circulating NKT cell numbers on day 1 (FIG. 2A) indicates in vivo NKT activation and homing to tissues with interferon-γ release in situ, thereby accounting for an increase in IP-10. The other two cytokines (IL-12 and MIP-1β) were likely to be released in vivo by antigen presenting myeloid cells.

Figure 5A:
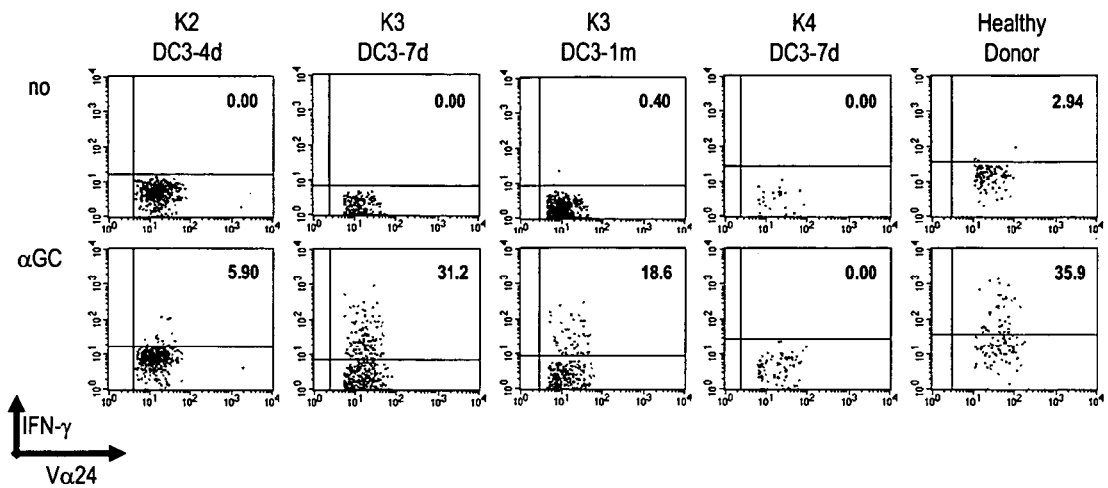
FIG. 5 demonstrates functional analysis of freshly isolated NKT cells mobilized in vivo. (A) Intracellular cytokine staining for α-GalCer reactive interferon-γ production. Freshly isolated PBMCs from post vaccination samples containing NKT cells or healthy donors were cultured overnight with anti-CD28 alone (as control), or with 100 ng/ml α-GalCer (α-GC) in the presence of monensin. The percent of interferon-γ producing Vα24+Vβ11+ cells was quantified by flow cytometry. (B) Detection of α-GalCer reactive interferon-γ producing cells by Elispot. Freshly isolated PBMCs from pre or post vaccination samples were cultured overnight with 100 ng/ml α-GalCer (α-GC). The presence of interferon-γ producing cells was quantified by Elispot.
Figure 5B:
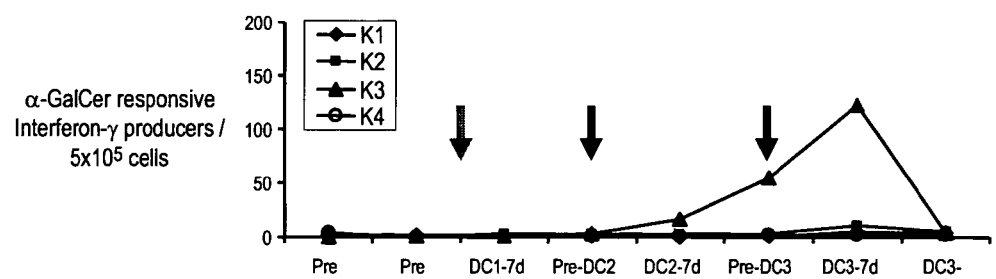

Circulating NKT cells from healthy humans respond to α-GalCer with rapid production of interferon-γ in vitro. Since DC vaccination led to an increase in NKT cells to within the range seen in healthy donors, the ability of these cells to secrete IFN-γ in vitro was assessed, using Elispot and ICS. In both assays, freshly isolated NKT cells mobilized in vivo produced little detectable IFN-γ, with the exception of some time points in one patient (K3; FIGS. 5A, 5B). Therefore, freshly isolated circulating NKT cells expanded in vivo seemed to be impaired in their ability to secrete IFN-γ, similar to that reported previously for naturally occurring NKT cells in patients with myeloma and other advanced cancers.

A lack of IFN-γ production may be associated with the production of other cytokines. For example in mice, IL-13 producing NKT cells have immune regulatory properties. Production of alternate cytokines was therefore analyzed by two methods. An analysis of supernatants from overnight cultures of PBMCs pre-versus post vaccination confirmed the lack of increase in interferon-γ or the chemokine IP-10 (normally produced in response to IFN-γ; not shown). No increase in IL-4, IL-10, IL-13, and IL-2 was noted in these supernatants (not shown). RNA isolated from these cells was also analyzed for IFN-γ, IL-4 and IL-13 transcripts by TaqMan, and again confirmed the data from other assays (not shown). Therefore, NKT cells mobilized in vivo in blood after α-GalCer DC injection were less efficient at rapid interferon-γ production in response to α-GalCer restimulation in short term assays, compared to those from healthy donors.

Figure 6A:
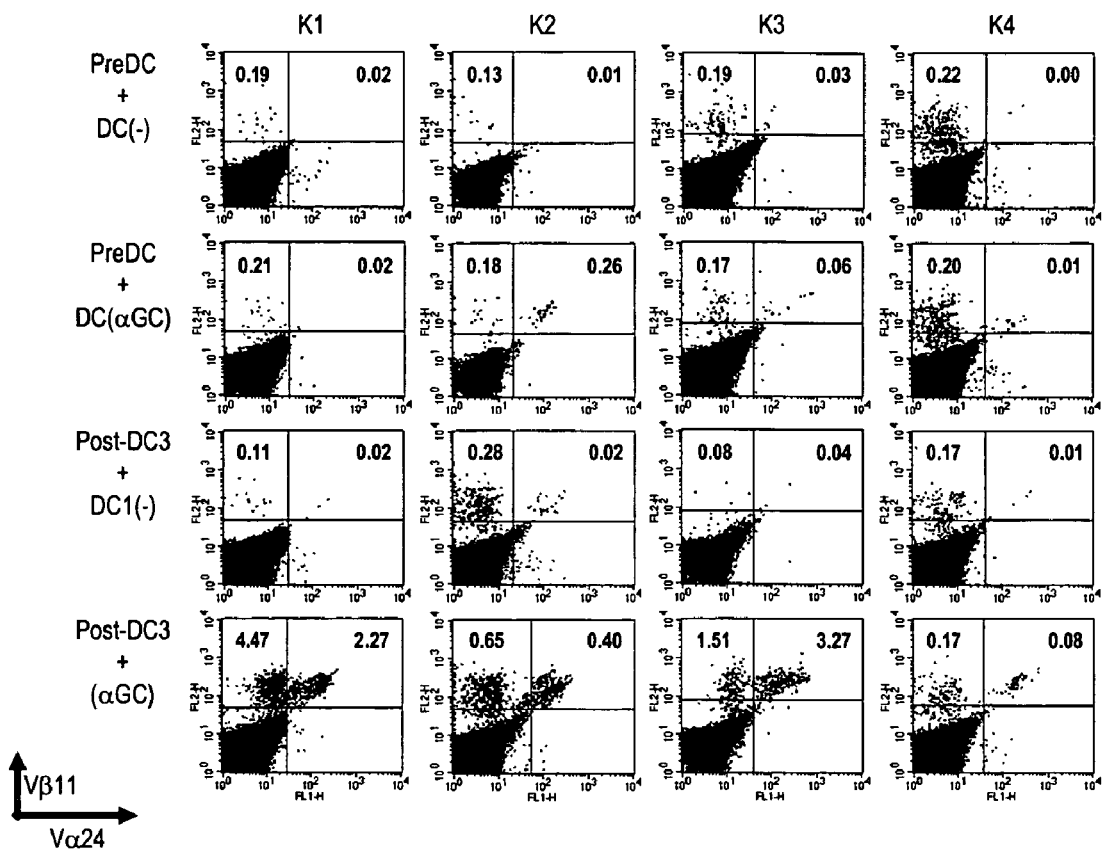
FIG. 6 demonstrates the proliferative capacity and function of mobilized NKT cells. (A) DC mediated expansion of mobilized NKT cells in vitro. Pre and post immunization PBMCs were thawed together and cultured with autologous monocyte derive mature DCs with or without pulsing with 100 ng/ml α-GalCer (DC:responder ratio of 1:20), in the presence of 50 U/ml IL-2. After 7 days of culture, the presence of Vα24+Vβ11+ iNKT cells was quantified by flow cytometry. Numbers in the quadrant indicates the percent of cells in the quadrant of the total lymphocyte population. (B) Binding of iNKT cells expanded in vitro from post vaccine samples to CD1d-α-GalCer dimers. Dimer(−) refers to unloaded dimers. Expression of V□24 or V□11 on dimer binding cells was analyzed by flow cytometry. (C) Interferon-γ production by ex vivo expanded NKT cells. NKT cells expanded ex vivo as in FIG. 6A were stimulated overnight with unpulsed or α-GalCer pulsed autologous DCs in the presence of monensin. NKT cells expanded from healthy donors were used as a control. The presence of interferon-γ producing cells was quantified by flow cytometry. (D) Taqman analysis of cytokine secretion in expanded NKT cells. NKT cells expanded ex vivo as in FIG. 6A were stimulated overnight with unpulsed or α-GalCer pulsed autologous DCs. NKT cells expanded from healthy donors were used as a control. The presence of mRNA for selected cytokines (interferon-γ, IL-4, IL-10, and IL-13) was analyzed by real time RT-PCR. Data were normalized to the expression of a housekeeping gene, GAPDH. α-GalCer reactive transcription was analyzed by comparing the expression in control versus α-GalCer stimulated samples. * $p<0.05$ for comparison with healthy donor control.
Figure 6B:
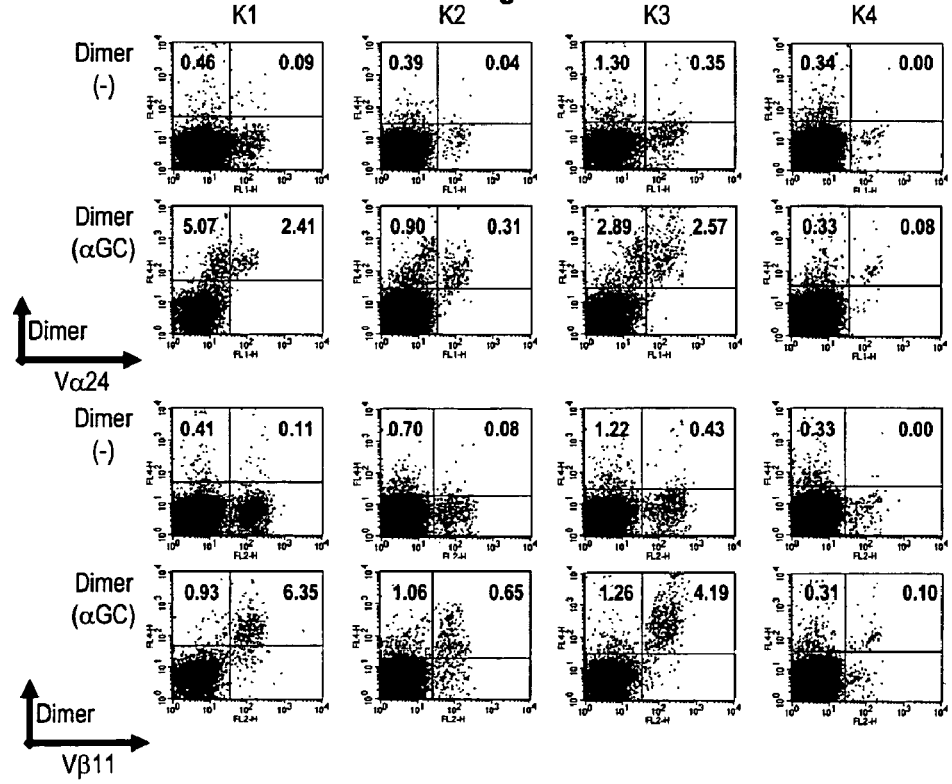
Figure 6C:
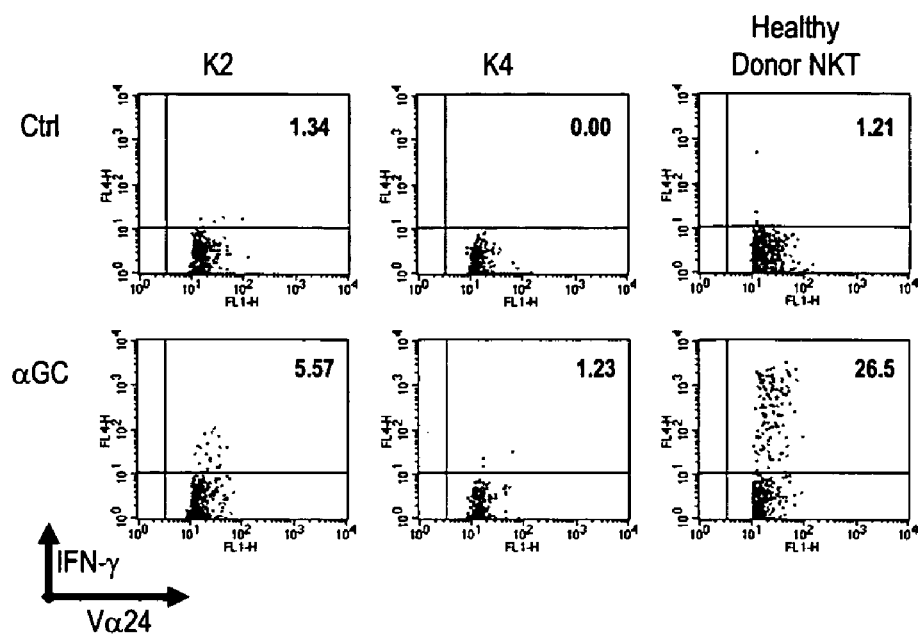
Figure 6D:
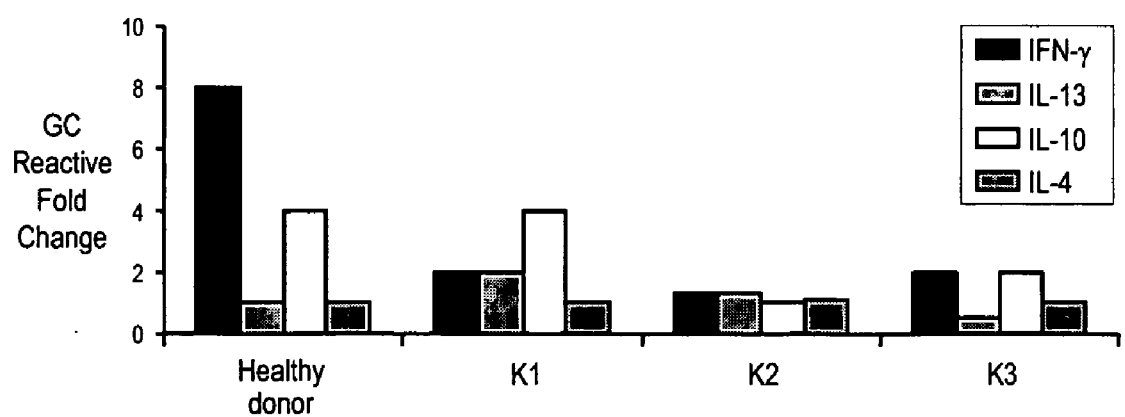

Human NKT cells readily undergo several fold expansion in vitro after stimulation with α-GalCer pulsed mature DCs to yield NKT cells with a Th1 phenotype. To test the proliferative capacity of mobilized NKT cells, pre- and post-immunization PBMCs were cultured with α-GalCer loaded DCs. Minimal NKT expansion was seen in preimmunization samples, consistent with a severe deficiency of NKT cells at baseline. In contrast, NKT cells could be readily expanded from post vaccine samples in just one week cultures (FIG. 6A). The expanded NKT cells were again both Vα24+/α-GalCer-dimer+ and Vα24−/α-GalCer-dimer+, as in the case of freshly isolated NKT cells (FIG. 6B). Interestingly, even when these expanded NKT cells were stimulated in vitro with α-GalCer loaded DCs, they exhibited reduced capacity for IFN-γ secretion, compared to their counterparts from healthy controls (FIG. 6C). This was again confirmed by TaqMan analysis (FIG. 6D).

Example 4

Antigen-Specific T Cell Responses

The increase in serum IL-12 after α-GalCer/DC vaccination suggested the possibility that NKT activation might lead to the activation of APCs in vivo, which might in turn enhance antigen specific CD8+ killer T cell responses. To assess changes in antigen specific T cells, viral antigen specific T cells against influenza matrix protein and CMVpp65 were monitored by Elispot and MHC tetramers. This was feasible as all patients were HLA A2+. An increase in CMV pp65-specific, but not influenza MP-specific interferon-γ producers in fresh PBMCs was observed in 3 of 4 patients following injection of α-GalCer pulsed, but not unpulsed DCs (FIG. 7A). This was also accompanied by a modest increase in peptide-MHC tetramer binding cells (not shown).

Figure 7C:
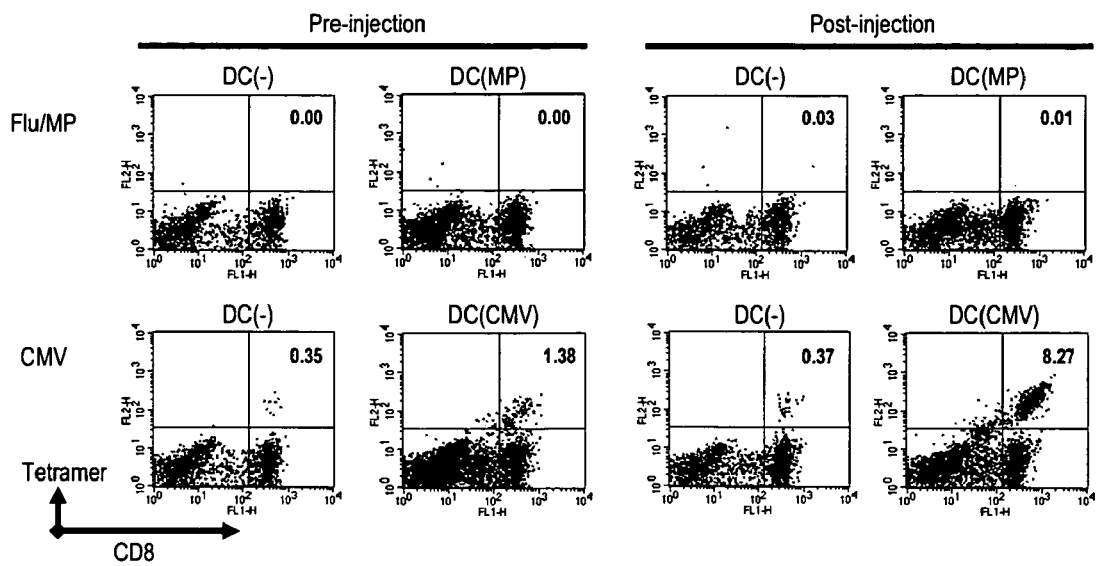
FIG. 7 demonstrates the changes elicited in antigen specific T cell responses. (A) Changes in CMV-pp65 and Flu-MP specific interferon-γ producing T cells. Freshly isolated PBMCs were cultured overnight with defined A2 restricted peptides from Flu-MP or CMVpp65. The number of antigen specific interferon-γ producing T cells was measured using an Elispot assay. (B) Expansion of virus specific memory T cells (Recall tetramer assay). Samples from pre or post immunization samples were thawed together and cocultured with autologous mature DCs pulsed with specific peptides. After 7 days of culture, the number of peptide specific MHC tetramer binding T cells was quantified by flow cytometry. Number indicates percent of tetramer positive cells in the quadrant. * $p<0.05$ on comparison with preimmunization value. (C) Representative FACS plots showing staining for CMVpp65-HLA A2 tetramer and Flu-MP-A2 tetramer, from an expansion as in FIG. 7B. (D) Changes in Flu-MP specific memory T cells in a patient who also received an inactivated influenza vaccine during the course of the trial. Pre and post immunization T cells were thawed together and expanded with autologous peptide pulsed DCs as in FIG. 7B. After 7 days of culture, the presence of Flu-MP-A2 tetramer binding T cells was monitored by flow cytometry.

To assess memory T cells, PBMCs from before and after immunization were thawed together and expanded using peptide loaded DCs. Antigen specific T cell expansion was monitored using MHC tetramers. Injection of α-GalCer loaded DCs was associated with an increase in CMV specific memory T cells, but not Flu-MP specific T cells in all three individuals tested (FIGS. 7B, 7C).

Figure 7D:
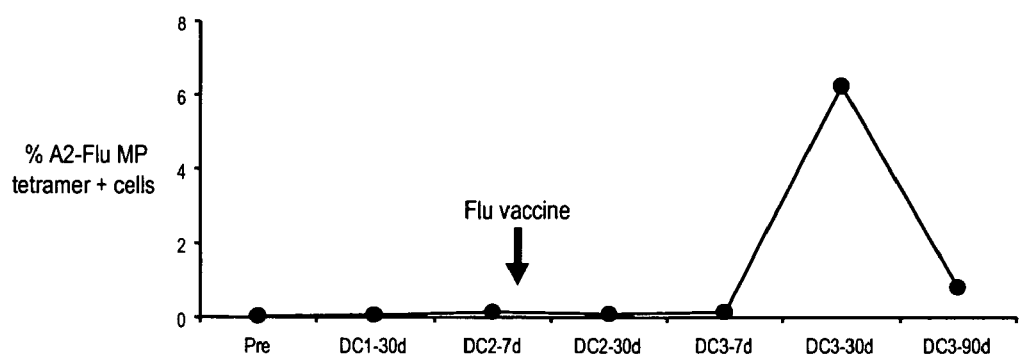

One of the patients on the study (K2) received an inactivated influenza vaccine as a part of routine care, shortly after the injection of α-GalCer loaded DCs. These vaccines are traditionally thought to be poor at activating CD8+ killer T cell responses and mostly boost only humoral immunity. Surprisingly, there was a significant expansion of Flu-MP specific, interferon-γ producing and memory T cells in this patient, consistent with enhancement of vaccine induced immune response due to α-GalCer pulsed DCs (FIG. 7D).

Figure 8:
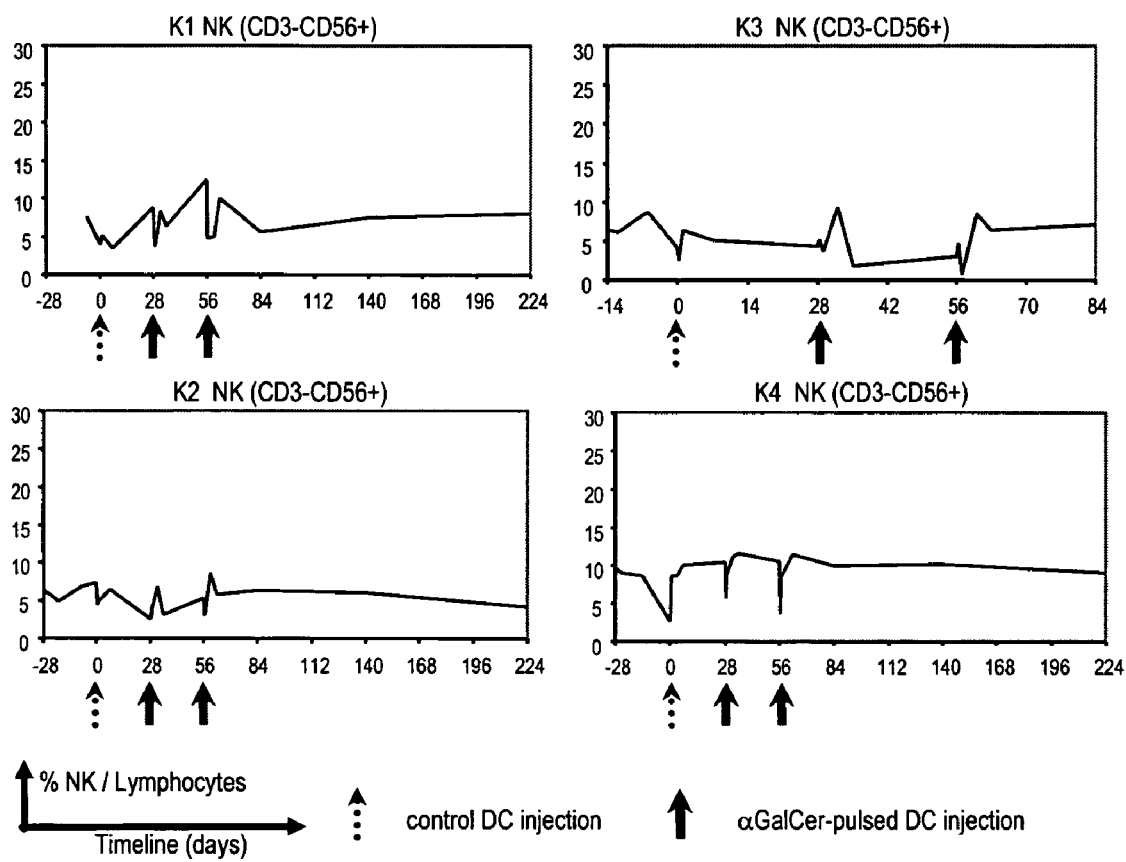
FIG. 8 demonstrates changes elicited in NK cells. The number of CD3− CD56+ NK cells in fresh PBMCs was monitored by flow cytometry, before and after DC vaccination.

A mild transient decline in circulating NK cell numbers at 6 or 24 hours was noted after all vaccines. The cause of this decline in NK cells is not clear, however it did not differ between unpulsed or α-GalCer pulsed DCs. In two patients (K2 and K3), there was a transient spike in NK numbers (and both $CD16^+$ and $CD16^- CD56^{hi}$ subsets) after α-GalCer DCs. However, this was within the inter-assay variance seen at baseline (FIG. 8). There was no detectable up-regulation of CD69 on NK cells/subsets, and no changes in the expression of natural cytotoxicity receptors p30, p44 and p46 on NK cells/subsets after DC vaccination (not shown). There was also no detectable increase in interferon-γ production in CD3− population enriched in NK cells post vaccination.

It will be appreciated by a person skilled in the art that the present invention is not limited by what has been particularly shown and described hereinabove. Rather, the scope of the invention is defined by the claims that follow:

What is claimed is:

1. A method for expanding an NKT cell population, said method comprising:
    a) generating a cytokine mediated matured dendritic cell population by subjecting immature dendritic cells to a cytokine cocktail comprising IL-1β, IL-6, TNF-α, and $PGE_2$;
    b) contacting the matured dendritic cells with KRN-7000 to reach at least a 60% maturity as expressed by % CD83+ cells, and
    c) contacting the cells in (b) with an NKT cell population,
    d) expanding the NKT cell population in said subject to at least 100 NKT cells per 1×10⁶ lymphocytes in peripheral blood.

2. The method of claim 1, wherein said KRN-7000 is at a concentration ranging from 1-1,000 ng/ml.

3. The method of claim 1, wherein said dendritic cells are present in or isolated from a subject having a carcinoma or myeloma.

4. A method for expanding an NKT cell population in vivo, said method comprising:
    a) generating a cytokine mediated matured dendritic cell population by subjecting immature dendritic cells to a cytokine cocktail comprising IL-1β, IL-6, TNF-α, and $PGE_2$;
    b) contacting the matured dendritic cells with KRN-7000 to reach at least a 60% maturity as expressed by % CD83+ cells, and
    c) administering the cells in (b) to a subject,
    d) allowing the contacting of said cells in (b) with the NKT cell population of said subject, whereby said NKT cell population undergoes expansion in said subject for a period of at least two months, following the administering step (b).

5. The method of claim 4, wherein said KRN-7000 is at a concentration ranging from 1-1,000 ng/ml.

6. The method of claim 4, wherein said dendritic cells are present in or isolated from a subject having a carcinoma or myeloma.

7. A method for stimulating or enhancing an immune response in a subject, said method comprising:
    a) generating a cytokine mediated matured dendritic cell population by subjecting immature dendritic cells to a cytokine cocktail comprising IL-1β, IL-6, TNF-α, and $PGE_2$;
    b) contacting the matured dendritic cells with KRN-7000 to reach at least a 60% maturity as expressed by % CD83+ cells, and
    c) administering the cells in (b) to a subject,
    d) allowing the contacting of said cells in (b) with the NKT cell population of said subject, whereby said NKT cell population undergoes expansion to yield at least 100 NKT cells per 1×10⁶ lymphocytes in peripheral blood of said subject and said NKT cell population participates in said immune response.

8. The method of claim 7, wherein said KRN-7000 is at a concentration ranging from 1-1000 ng/ml.

9. The method of claim 7, wherein said dendritic cells are isolated from a subject having a carcinoma or myeloma.

10. The method of claim 7, wherein said immature dendritic cells are isolated from a subject with an infection or a disease.

11. The method of claim 10, wherein said infection is viral.

12. The method of claim 7, further comprising the step of contacting said NKT cell population in (d) with a second antigen presenting cell.

13. The method of claim 12, further comprising the step of contacting said NKT cell population with a vaccine.

14. The method of claim 13, wherein said vaccine comprises antigens derived from a pathogen.

15. The method of claim 13, wherein said vaccine comprises antigens predominantly or preferentially expressed in neoplastic cells or tissue.

16. A method for suppressing or reducing the severity of a tumor in a subject, comprising the steps of:
    a) isolating immature dendritic cells from a subject having tumor,
    b) generating a cytokine mediated matured dendritic cell population by subjecting said immature dendritic cells to a cytokine cocktail comprising IL-1β, IL-6, TNF-α, and $PGE_2$;
    c) contacting the matured dendritic cells with KRN-7000 to reach at least a 60% maturity as expressed by % CD83+ cells, and
    d) administering the cells in (c) to a subject,
    e) allowing the contacting of said cells in (c) with the NKT cell population of said subject, whereby said NKT cell population undergoes expansion to yield at least 100 NKT cells per 1×10⁶ lymphocytes in peripheral blood of said subject and said NKT cells participate in an antineoplastic response in said subject.

17. The method of claim 16, wherein said subject is post at least one course of cancer therapy and has preneoplastic or hyperplastic cells or tissue.

18. The method of claim 16, wherein said subject is immunosuppressed or immunocompromised.

* * * * *